US012569541B2

(12) United States Patent
Okada et al.

(10) Patent No.: US 12,569,541 B2
(45) Date of Patent: Mar. 10, 2026

(54) STEM CELLS FOR TRANSPLANTATION AND MANUFACTURING METHOD THEREFOR

(71) Applicant: NATIONAL CENTER OF NEUROLOGY AND PSYCHIATRY, Kodaira (JP)

(72) Inventors: Takashi Okada, Tokyo (JP); Yuko Kasahara, Tokyo (JP); Shinichi Takeda, Tokyo (JP)

(73) Assignee: NATIONAL CENTER OF NEUROLOGY AND PSYCHIATRY, Tokyo (JP)

( * ) Notice: Subject to any disclaimer, the term of this patent is extended or adjusted under 35 U.S.C. 154(b) by 110 days.

(21) Appl. No.: 16/821,630

(22) Filed: Mar. 17, 2020

(65) Prior Publication Data

US 2020/0222506 A1     Jul. 16, 2020

Related U.S. Application Data

(63) Continuation of application No. 15/966,917, filed on Apr. 30, 2018, now abandoned, which is a continuation of application No. 14/892,474, filed as application No. PCT/JP2014/063448 on May 21, 2014, now abandoned.

(30) Foreign Application Priority Data

May 22, 2013     (JP) ................................. 2013-108408

(51) Int. Cl.
| | |
|---|---|
| *A61K 38/20* | (2006.01) |
| *A61K 35/28* | (2015.01) |
| *A61L 27/38* | (2006.01) |
| *C07K 14/54* | (2006.01) |
| *C12N 5/0775* | (2010.01) |
| *C12N 7/00* | (2006.01) |
| *C12N 15/86* | (2006.01) |
| *A61K 48/00* | (2006.01) |

(52) U.S. Cl.
CPC .......... *A61K 38/2066* (2013.01); *A61K 35/28* (2013.01); *A61L 27/3834* (2013.01); *C07K 14/5428* (2013.01); *C12N 5/0662* (2013.01); *C12N 5/0663* (2013.01); *C12N 7/00* (2013.01); *C12N 15/86* (2013.01); *A61K 48/00* (2013.01); *C12N 2501/231* (2013.01); *C12N 2510/00* (2013.01); *C12N 2510/02* (2013.01); *C12N 2750/14143* (2013.01); *C12N 2750/14171* (2013.01)

(58) Field of Classification Search
CPC .... A61K 38/2066; A61K 35/28; A61K 48/00; A61L 27/3834; C07K 14/5428; C12N 5/0662; C12N 5/0663; C12N 7/00; C12N 15/86; C12N 2501/231; C12N 2510/00; C12N 2510/02; C12N 2750/14143; C12N 2750/14171; A61P 9/00
See application file for complete search history.

(56) References Cited

U.S. PATENT DOCUMENTS

| | | | |
|---|---|---|---|
| 5,486,359 A | 1/1996 | Caplan et al. | |
| 6,398,816 B1 | 6/2002 | Breitbart et al. | |
| 2006/0002906 A1* | 1/2006 | Chiu ...................... | A61P 37/00 |
| | | | 435/372 |
| 2007/0122377 A1* | 5/2007 | Best ...................... | A61P 37/04 |
| | | | 514/48 |
| 2008/0249050 A1 | 10/2008 | Engelhardt et al. | |
| 2010/0111905 A1* | 5/2010 | Balber ................... | A61P 19/04 |
| | | | 424/93.7 |
| 2013/0071920 A1 | 3/2013 | Kitamura et al. | |

FOREIGN PATENT DOCUMENTS

| | | |
|---|---|---|
| EP | 1591523 A4 | 7/2007 |
| JP | 2002-511094 | 4/2002 |
| JP | 2005-531507 | 10/2005 |
| JP | 2009-534394 | 9/2009 |
| JP | 2011-251925 A | 12/2011 |
| JP | 2012-100599 A | 5/2012 |
| JP | 2012-157263 A | 8/2012 |
| WO | WO 99/03973 | 1/1999 |
| WO | WO 01/32189 A1 | 5/2001 |
| WO | WO 03/073998 A2 | 9/2003 |
| WO | WO 2007/124148 A2 | 11/2007 |

(Continued)

OTHER PUBLICATIONS

Min et al. "IL-10-transduced bone marrow mesenchymal stem cells can attenuate the severity of acute graft-versus-host disease after experimental allogeneic stem cell transplantation."Bone Marrow Transplant . May 2007;39(10):637-45. (Year: 2007).*

(Continued)

*Primary Examiner* — Titilayo Moloye

(74) *Attorney, Agent, or Firm* — Lisa Mueller; Casimir Jones SC

(57) ABSTRACT

It is intended to provide MSCs for transplantation that have an improved post-transplantation cell survival rate and engraftment rate and are highly safe with fewer adverse reactions, and a method for conveniently producing MSCs for transplantation having a high cell survival rate and engraftment rate. As means therefor, the present invention provides a stem cell for transplantation comprising an MSC capable of overexpressing IL-10.

6 Claims, 15 Drawing Sheets

Specification includes a Sequence Listing.

(56)                 References Cited

FOREIGN PATENT DOCUMENTS

WO      WO2012/051210 A2      4/2012
WO      WO2014/189071        11/2014

OTHER PUBLICATIONS

Chen et al. "IL10—Transduced Mesenchymal Stem Cells Improve the Acute Graft-Versus-Host Disease Protection in a Murine Model." Blood (2007) 110 (11): 3242. (Year: 2007).*

Mielcarek et al. "Mesenchymal Stromal Cells Fail to Prevent Acute Graft-versus-Host Disease and Graft Rejection after Dog-Leukocyte-Antigen Haploidentical Bone Marrow Transplantation."Biol Blood Marrow Transplant. Feb. 2011; 17(2): 214-225. (Year: 2011).*

Renner et al. "Mesenchymal Stem Cells Require a Sufficient, Ongoing Immune Response to Exert Their Immunosuppressive Function." Transplant Proc.Jul. 2009-Aug. 41(6):2607-11. (Year: 2009).*

Gangadharan et al. "High-level expression of porcine factor VIII from genetically modified bone marrow-derived stem cells." Blood (2006) 107 (10): 3859-3864. (Year: 2006).*

Papadopoulou et al. "Mesenchymal stem cells are conditionally therapeutic in preclinical models of rheumatoid arthritis." Ann Rheum Dis . Oct. 2012;71(10):1733-40. (Year: 2012).*

Merino et al. "The Timing of Immunomodulation Induced by Mesenchymal Stromal Cells Determines the Outcome of the Graft in Experimental Renal Allotransplantation." Cell Transplant . Jun. 9, 2017;26(6):1017-1030. (Year: 2017).*

Vangala et al. "Genetic modification of mesenchymal stem cells to enhance their anti-tumor efficacy." Asia-Pacific Journal of Oncology 2021, 2: 1-6. (Year: 2021).*

Wold et al. "Adenovirus Vectors for Gene Therapy, Vaccination and Cancer Gene Therapy." Curr Gene Ther. Dec. 2013 ; 13(6): 421-433. (Year: 2013).*

Podesta et al. "Mesenchymal Stromal Cells for Transplant Tolerance." Front Immunol. 2019; 10: 1287. (Year: 2019).*

Uder et al. "Mammalian MSC from selected species: Features and applications." Cytometry A . Jan. 2018;93(1):32-49. (Year: 2018).*

Rajapaksha et al. 'Adeno-Associated Virus (AAV)-Mediated Gene Therapy for Disorders of Inherited and Non-Inherited Origin'. In Vivo and Ex Vivo Gene Therapy for Inherited and Non-Inherited Disorders, IntechOpen, Mar. 13, 2019. Crossref, doi: 10.5772/intechopen.80317. (Year: 2019).*

Ge et al. "Factors influencing the development of an anti-factor IX (FIX) immune response following administration of adeno-associated virus-FIX." Blood.Jun. 15, 2001;97(12):3733-7. (Year: 2001).*

Rivière, et al. "Long-term expression and repeated administration of AAV type 1, 2 and 5 vectors in skeletal muscle of immunocompetent adult mice." Gene Therapy vol. 13, pp. 1300-1308 (2006) (Year: 2006).*

Halbert et al. "Repeat Transduction in the Mouse Lung by Using Adeno-Associated Virus Vectors with Different Serotypes" J Virol. Feb. 2000;74(3): 1524-1532 (Year: 2000).*

Costa-Verdera et al. "Understanding and Tackling Immune Responses to Adeno-Associated Viral Vectors." Hum Gene Ther . Sep. 2023;34(17-18):836-852. (Year: 2023).*

Takeda, S., "Development of Cell Transplantation Therapy for Muscular Dystrophy Using Bone Marrow Stroma-Derived Progenitor Cells and Muscular Dystrophy-Affected Dogs," *Health Labour Sciences Research Grant, Comprehensive/Shared Study Report,* 2007, (partial English Translation), 10 pages (2008).

Connick, P. et al., "Autologous Mesenchymal Stem Cells for the Treatment of Secondary Progressive Multiple Sclerosis: An Open-Label Phase 2a Proof-of Concept Study", *Neurology,* vol. 11, pp. 150-156 (Feb. 2012).

Carrancio, S. et al., "Effects of MSC Coadministration and Route of Delivery on Cord Blood Hematopoietic Stem Cell Engraftment," *Cell Transplantation,* vol. 22, pp. 1171-1183 (2013).

Von Bonin, M. et al., "Treatment of Refractory Acute GVHD with Third-Party MSC Expanded in Platelet Lysate-Containing Medium," *Bone Marrow Transplantation,* vol. 43, pp. 245-251 (2009).

Tolar, J. et al., "Mesenchymal Stromal Cells for Graft-Versus-Host Disease," *Human Gene Therapy,* vol. 22, pp. 257-262 (Mar. 2011).

Si, Y. et al., "MSCs: Biological Characteristics, Clinical Applications and Their Outstanding Concerns," *Ageing Research Reviews,* vol. 10, pp. 93-103 (2011).

Wang, S. et al., "Clinical Applications of Mesenchymal Stem Cells," *Journal of Hematoloqy & Oncology,* vol. 5, No. 19, pp. 1-9 (2012).

Kasahara, Y. et al., "Engraftment of Mesenchymal Stromal Cells That Can Differentiate to Form Myogenic Cells is Enhanced by Expressing IL-10 in Dog with Duchenne Muscular Dystrophy," *Molecular Therapy,* vol. 21, Supplement 1, 3 pages (May 2013).

Min, C. et al., "IL-10-Transduced Bone Marrow Mesenchymal Stem Cells Can Attenuate the Severity of Acute Graft-Versus-Host Disease After Experimental Allogeneic Stem Cell Transplantation," *Bone Marrow Transplantation,* 39:637-645 (2007).

Manning, E. et al., "Interleukin-10 Delivery Via Mesenchymal Stem Cells: A Novel Gene Therapy Approach to Prevent Lung Ischemia-Reperfusion Injury," *Human Gene Therapy,* 21:713-727 (Jun. 2010).

Yang, J. et al., "Adult Neural Stem Cells Expressing IL-10 Confer Potent Immunomodulation and Remyelination in Experimental Autoimmune Encephalitis," *The Journal of Clinical Investigation,* vol. 119, No. 12, pp. 3678-3691 (Dec. 2009).

Brikci-Nigassa, L. et al., "Prope Tolerance to Heart Allografts in Mice Associated With Persistence of Donor Interleukin-10-Transduced Stem Cells," *Transplantation Journal,* vol. 93, No. 8, pp. 761-768 (Apr. 27, 2012).

Hase, T. et al., "Effect of IL-10 to Prolong Organ Engraltment Period in Mouse Cardiac Transplantation Models," *Acta Urol. Jpn.,* vol. 51, No. 6, 4 pages (Jun. 30, 2005; with Enqlish abstract).

Nitahara-Kasahara, Y et al., "Long-Term Engraltment of Multipotent Mesenchymal Stromal Cells That Differentiate to Form Myogenic Cells in Dogs With Duchenne Muscular Dystrophy," *Molecular Therapy,* vol. 20, No. 1, pp. 168-177 (Jan. 2012).

American Society of Gene & Cell Therapy 16th Annual Meeting, 18 pages (May 15-18, 2013).

American Society of Gene & Cell Therapy 16th Annual Meeting-Final Program, 8 pages (May 15-18, 2013).

Choi et al., "Mesenchymal stem cells overexpressing interleukin-10 attenuate collagen-induced arthritis in mic," *Clinical and Experimental Immunology,* 153(2):269-276 (2008).

Payne et al., "Human adipose-derived mesenchymal stem cells engineered to secrete IL-10 inhibit APC function and limit CNS autoimmunity," *Brain, Behavior and Immunity,* 30:103-114 (2013).

Supplementary European Search Report received in European Patent Application No. EP 14 80 0673 dated Jan. 13, 2017.

Office Action received in U.S. Appl. No. 14/892,474 dated Sep. 8, 2016.

Office Action received in U.S. Appl. No. 14/892,474 dated Apr. 11, 2017.

Office Action received in U.S. Appl. No. 14/892,474 dated Oct. 4, 2017.

Office Action received in U.S. Appl. No. 14/892,474 dated Jan. 30, 2018.

Chen et al., "Freeze-thaw increases adeno-associated virus transduction of cells," *Am J. Physiol Cell Physiol,* 291 :C386-C392 (2006).

Overview of ELISA, Thermo Fisher Scientific, https://www.thermofisher.com, printed Oct. 1, 2017.

Gold et al., "Understanding pathogenesis and therapy of multiple sclerosis via animal models: 70 years of merits and culprits in experimental autoimmune encephalomyelitis research," *Brain,* 129:1953-1971 (2006).

Payne Natalie, et al., "Amelioration of experimental autoimmune encephalomyelitis by human adipose derived mesenchymal stem cells overexpressing interleukin-10," *Journal of Neuroimmunology,* 228(1):1-219 (2010).

International Search Report and English translation thereof of corresponding International Application No. PCT/JP2014/063448 dated Aug. 26, 2014, 8 pages.

Office Action received in U.S. Appl. No. 14/892,474, dated Jul. 1, 2016.

(56) References Cited

OTHER PUBLICATIONS

Office Action received in U.S. Appl. No. 14/892,474, dated Jul. 14, 2017.

Reporting letter received from Japanese associate dated Feb. 20, 2019 reporting the issuance of an Office Action for the Japanese Patent Application No. 2015-518272, dated Jan. 22, 2019.

Office Action and Search Report (in Japanese) received in Japanese Patent Application No. 2015-518272, dated Jan. 22, 2019.

Office Action dated Dec. 17, 2018 in U.S. Appl. No. 15/965,634 (copy enclosed).

Definition of Transduction. NIH U.S. National Library of Medicine. Date Established: Jan. 1, 1968; Date of Entry: Jan. 1, 1999 (copy enclosed).

Natalie et al. "Amelioration of experimental autoimmune encephalomyelitis by human adipose derived mesenchymal stem cells overexpressing interleukin-10," 10th International Congress of neuroimmunology, vol. 228, Issues 1-2, Poster Sessions, Poster No. 41, p. 149 (Nov. 15, 2010) (copy enclosed).

Office Action dated May 29, 2019 received in U.S. Appl. No. 15/965,634.

Chen, S., et al., "Freeze-thaw increases adeno-associated virus transduction of cells," *Am J Physiol Cell Physiol*, 291:C386-C392 (2006).

Nitahara-Kasahara, Y., et al., "Cell Therapeutic Approach to Duchenne Muscular Dystrophy Using Myogenic Differentiation of Multipotent Mesenchymal Stromal Cells," *Molecular Therapy*, 17(1):S204-S205 (2009).

Office Action dated Dec. 20, 2019 received in U.S. Appl. No. 15/966,917.

Diekman, et al., "Intra-articular delivery of purified mesenchymal stem cells from C57BL/6 or MRL/MpJ superhealer mice prevents posttraumatic arthritis," *Cell Transplant.*, 22(8):1395-408 (2013), e published Aug. 10, 2012 (2012).

Office Action dated May 14, 2019 received in U.S. Appl. No. 15/966,917.

Holladay, et al. "Functionalized scaffold-mediated interleukin 10 gene delivery significantly improves survival rates of stem cells in vivo," *Mol Ther.*, May 2011; 19(5):969-78. doi: 10.1038/mt.2010. 311. Epub Jan. 25, 2011. (2011).

Kasahara, Y.N., et al., "176. Engraftment of Mesenchymal Stromal Cells That Can Differentiate To Form Myogenic Cells Is Enhanced by Expressing IL-10 in Dog with Duchenne Muscular Dystrophy,"

*Musculo-Skeletal Gene & Cell Therapy*, 11 vol. 21, Supplement 1, S69, May 1, 2013 (2013).

Office Action dated Dec. 26, 2018 received in U.S. Appl. No. 15/966,917.

Office Action dated Sep. 17, 2018 received in U.S. Appl. No. 15/966,917.

Franco-Guo, et al., "696. Immunomodulatory Effects of MSCs and IL-10 Gene Transfer in a Liver Transplantation Rejection Model," *Molecular Therapy*, vol. 17, S266. May 2009 (2009).

Extended European Search Report in Europe Application No. 20150966.8, dated Apr. 6, 2020, 9 pages.

Hayashita-Kinoh, "764. Immune Tolerance Induction in Canine X-Linked Muscular Dystrophy with rAAV9-Microdystrophin Transduction", Molecular Therapy volume Copyright, The American Society of Gene & Cell Therapy, dated Jan. 1, 2011, XP055675984, and Hayashita-Kinoh, "177. Molecular Therapy Musculo-Skeletal Gene & Cell Therapy I, 177. rAAV9-Mediated Microdystrophin Gene Transfer with Immune Tolerance Induction Improves Dystrophic Phenotype of Canine X-Linked Muscular Dystrophy", Copyright the American Society of Gene & Cell Therapy, dated Jan. 1, 2012, XP055675989, 2 pages.

J-H Shin et al., "Improvement of Cardiac Fibrosis in Dystrophic Mice by rAAV9-Mediated Microdystrophin Transduction", Gene Therapy, vol. 18, No. 9, dated Mar. 31, 2011, XP055152487, 10 pages.

Okada et al., "Current Challenges and Future Directions in Recombinant AAV-Mediated Gene Therapy of Duchenne Muscular Dystrophy", Pharmaceuticals, vol. 6, No. 7, dated Jun. 27, 2013, pp. 813-836, XP055152704, 24 pages.

Yur-Ren Kuo et al., "Mesenchymal Stem Cells as Immunomodulators in a Vascularized Composite Allotransplantation", Clinical & Developmental Immunology, vol. 2012, dated Jan. 1, 2012, XP055579207, 8 pages.

Federica Casiraghi et al., "Pretransplant Infusion of Mesenchymal stem Cells Prolongs the Survival of a Semiallogeneic Heart Transplant through the Generation of Regulatory T Cells", The Journal of Immunology, 181:3933-3946 (2008).

Shabbir et al. "Muscular Dystrophy Therapy by Nonautologous Mesenchymal Stem Cells: Muscle Regeneration Without Immunosuppression and Inflammation." Transplantation 87(9):p. 1275-1282, May 15, 2009. (Year: 2009).

Bostick et al. "Adeno-associated virus serotype-9 microdystrophin gene therapy ameliorates electrocardiogra abnormalities in mdx mice." Hum Gene Ther. Aug. 2008;19(8):851-6. (Year: 2008).

* cited by examiner

[Bar graph: y-axis labeled "IL-10 (pg/mL)" with values 0, 100, 200, 300, 400, 500, 600; x-axis categories "AAV1-GFP" and "AAV1-IL10". AAV1-IL10 bar reaches approximately 530 pg/mL.]

vIL-10(-)MSCs vIL-10(+)MSCs $(n=4\text{-}7, p<0.005)$

Donor
(normal dog)

Bone marrow collection

AAV-IL-10 (or AAV-GFP)
RV-Luciferase

Isolation and growth of CD271+MSCs

Recipient
(affected dog)

Transplantation to right and left
tibialis anterior muscles
Left: vIL-10(-)MSCs
Right: vIL-10(+)MSCs IL-10(+) MSCs anti Luc anti Luc anti Luc

SEQUENCE LISTING

<160> NUMBER OF SEQ ID NOS: 14

<210> SEQ ID NO 1
<211> LENGTH: 178
<212> TYPE: PRT
<213> ORGANISM: Homo sapiens

<400> SEQUENCE: 1

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 2
<211> LENGTH: 537
<212> TYPE: DNA
<213> ORGANISM: Homo sapiens

<400> SEQUENCE: 2

```
atgcacagct cagcactgct ctgttgcctg gtcctcctga ctggggtgag ggccagccca      60
ggccagggca cccagtctga gaacagctgc acccacttcc caggcaacct gcctaacatg     120
cttcgagatc tccgagatgc cttcagcaga gtgaagactt tctttcaaat gaaggatcag     180
ctggacaact tgttgttaaa ggagtccttg ctggaggact ttaagggtta cctgggttgc     240
caagccttgt ctgagatgat ccagttttac ctggaggagg tgatgcccca agctgagaac     300
caagacccag acatcaaggc gcatgtgaac tccctggggg agaacctgaa gaccctcagg     360
ctgaggctac ggcgctgtca tcgatttctt ccctgtgaaa acaagagcaa ggccgtggag     420
caggtgaaga atgcctttaa taagctccaa gagaaaggca tctacaaagc catgagtgag     480
tttgacatct tcatcaacta catagaagcc tacatgacaa tgaagatacg aaactga       537
```

<210> SEQ ID NO 3
<211> LENGTH: 178
<212> TYPE: PRT
<213> ORGANISM: Mus musculus

<400> SEQUENCE: 3

```
Met Pro Gly Ser Ala Leu Leu Cys Cys Leu Leu Leu Leu Thr Gly Met
1               5                   10                  15

Arg Ile Ser Arg Gly Gln Tyr Ser Arg Glu Asp Asn Asn Cys Thr His
            20                  25                  30

Phe Pro Val Gly Gln Ser His Met Leu Leu Glu Leu Arg Thr Ala Phe
```

-continued

```
               35                40                45
Ser Gln Val Lys Thr Phe Phe Gln Thr Lys Asp Gln Leu Asp Asn Ile
    50                55                60

Leu Leu Thr Asp Ser Leu Met Gln Asp Phe Lys Gly Tyr Leu Gly Cys
65                70                75                80

Gln Ala Leu Ser Glu Met Ile Gln Phe Tyr Leu Val Glu Val Met Pro
                85                90                95

Gln Ala Glu Lys His Gly Pro Glu Ile Lys Glu His Leu Asn Ser Leu
            100                105                110

Gly Glu Lys Leu Lys Thr Leu Arg Met Arg Leu Arg Arg Cys His Arg
            115                120                125

Phe Leu Pro Cys Glu Asn Lys Ser Lys Ala Val Glu Gln Val Lys Ser
    130                135                140

Asp Phe Asn Lys Leu Gln Asp Gln Gly Val Tyr Lys Ala Met Asn Glu
145                150                155                160

Phe Asp Ile Phe Ile Asn Cys Ile Glu Ala Tyr Met Met Ile Lys Met
                165                170                175

Lys Ser

<210> SEQ ID NO 4
<211> LENGTH: 537
<212> TYPE: DNA
<213> ORGANISM: Mus musculus

<400> SEQUENCE: 4
atgcctggct cagcactgct atgctgcctg ctcttactga ctggcatgag gatcagcagg      60
ggccagtaca gccgggaaga caataactgc acccacttcc cagtcggcca gagccacatg     120
ctcctagagc tgcggactgc cttcagccag gtgaagactt tctttcaaac aaaggaccag     180
ctggacaaca tactgctaac cgactcctta atgcaggact ttaagggtta cttgggttgc     240
caagccttat cggaaatgat ccagttttac ctggtagaag tgatgcccca ggcagagaag     300
catggcccag aaatcaagga gcatttgaat tccctgggtg agaagctgaa gaccctcagg     360
atgcggctga ggcgctgtca tcgatttctc ccctgtgaaa ataagagcaa ggcagtggag     420
caggtgaaga gtgattttaa taagctccaa gaccaaggtg tctacaaggc catgaatgaa     480
tttgacatct tcatcaactg catagaagca tacatgatga tcaaaatgaa aagctaa       537

<210> SEQ ID NO 5
<211> LENGTH: 178
<212> TYPE: PRT
<213> ORGANISM: Rattus norvegicus

<400> SEQUENCE: 5

Met Pro Gly Ser Ala Leu Leu Cys Cys Leu Leu Leu Leu Ala Gly Val
1                5                10                15

Lys Thr Ser Lys Gly His Ser Ile Arg Gly Asp Asn Asn Cys Thr His
            20                25                30

Phe Pro Val Ser Gln Thr His Met Leu Arg Glu Leu Arg Ala Ala Phe
            35                40                45

Ser Gln Val Lys Thr Phe Phe Gln Lys Lys Asp Gln Leu Asp Asn Ile
    50                55                60

Leu Leu Thr Asp Ser Leu Leu Gln Asp Phe Lys Gly Tyr Leu Gly Cys
65                70                75                80

Gln Ala Leu Ser Glu Met Ile Lys Phe Tyr Leu Val Glu Val Met Pro
                85                90                95
```

```
Gln Ala Glu Asn His Gly Pro Glu Ile Lys Glu His Leu Asn Ser Leu
            100                 105                 110

Gly Glu Lys Leu Lys Thr Leu Trp Ile Gln Leu Arg Arg Cys His Arg
        115                 120                 125

Phe Leu Pro Cys Glu Asn Lys Ser Lys Ala Val Glu Gln Val Lys Asn
        130                 135                 140

Asp Phe Asn Lys Leu Gln Asp Lys Gly Val Tyr Lys Ala Met Asn Glu
145                 150                 155                 160

Phe Asp Ile Phe Ile Asn Cys Ile Glu Ala Tyr Val Thr Leu Lys Met
                165                 170                 175

Lys Asn

<210> SEQ ID NO 6
<211> LENGTH: 538
<212> TYPE: DNA
<213> ORGANISM: Rattus norvegicus

<400> SEQUENCE: 6
catgcctggc tcagcactgc tatgttgcct gctcttactg gctggagtga agaccagcaa      60
aggccattcc atccggggtg acaataactg cacccacttc ccagtcagcc agacccacat     120
gctccgagag ctgagggctg ccttcagtca agtgaagact ttctttcaaa agaaggacca     180
gctggacaac atactgctga cagattcctt actgcaggac tttaagggtt acttgggttg     240
ccaagccttg tcagaaatga tcaagttttta cctggtagaa gtgatgcccc aggcagagaa     300
ccatggccca gaaatcaagg agcatttgaa ttccctggga gagaagctga gaccctctg     360 gatacagctg cgacgctgtc atcgatttct ccctgtgag aataaaagca aggcagtgga     420
gcaggtgaag aatgatttta ataagctcca agacaaaggt gtctacaagg ccatgaatga     480
gtttgacatc ttcatcaact gcatagaagc ctacgtgaca ctcaaaatga aaaattga     538

<210> SEQ ID NO 7
<211> LENGTH: 181
<212> TYPE: PRT
<213> ORGANISM: Canis lupus familiaris

<400> SEQUENCE: 7

Met His Gly Ser Ala Leu Leu Cys Cys Cys Leu Val Leu Leu Ala Gly
1               5                   10                  15

Val Gly Ala Ser Arg His Gln Ser Thr Leu Leu Glu Asp Asp Cys Thr
            20                  25                  30

His Phe Pro Ala Ser Leu Pro His Met Leu Arg Glu Leu Arg Ala Ala
        35                  40                  45

Phe Gly Arg Val Lys Ile Phe Phe Gln Met Lys Asp Lys Leu Asp Asn
        50                  55                  60

Ile Leu Leu Thr Gly Ser Leu Leu Glu Asp Phe Lys Ser Tyr Leu Gly
65                  70                  75                  80

Cys Gln Ala Leu Ser Glu Met Ile Gln Phe Tyr Leu Glu Glu Val Met
                85                  90                  95

Pro Arg Ala Glu Asn His Asp Pro Asp Ile Lys Asn His Val Asn Ser
            100                 105                 110

Leu Gly Glu Lys Leu Lys Thr Leu Arg Leu Arg Leu Arg Leu Arg Arg
        115                 120                 125

Cys His Arg Phe Leu Pro Cys Glu Asn Lys Ser Lys Ala Val Glu Gln
        130                 135                 140
```

-continued

```
Val Lys Ser Ala Phe Ser Lys Leu Gln Glu Lys Gly Val Tyr Lys Ala
145                 150                 155                 160

Met Ser Glu Phe Asp Ile Phe Ile Asn Tyr Ile Glu Thr Tyr Met Thr
                165                 170                 175

Met Arg Met Lys Ile
            180

<210> SEQ ID NO 8
<211> LENGTH: 546
<212> TYPE: DNA
<213> ORGANISM: Canis lupus familiaris

<400> SEQUENCE: 8
atgcatggct cagcactgct ctgttgctgc ctggtcctcc tggccggggt gggagccagc        60
cgacaccaga gcaccctact tgaggacgac tgcaccccact tcccagccag cctgccccac       120
atgctccgag agctccgagc tgccttcggg agggtgaaga tcttctttca aatgaaggac       180
aagctggaca acatactgct gaccgggtcc ctgctggagg actttaagag ttacctgggt       240
tgccaagccc tgtcggagat gatccagttt tacttggagg aggtgatgcc ccgggctgag       300
aaccacgacc cagacatcaa gaaccacgtg aactccctgg gagagaagct caagaccctc       360
aggctgagac tgaggctgcg acgctgtcac cgatttcttc cctgtgagaa taagagcaag       420
gcggtggagc aggtgaagag cgcatttagt aagctccagg agaaaggtgt ctacaaagcc       480
atgagtgagt ttgacatctt catcaactac atagaaacct catgacaat gaggatgaaa       540 atctga                                                                   546

<210> SEQ ID NO 9
<211> LENGTH: 178
<212> TYPE: PRT
<213> ORGANISM: Pan troglodytes

<400> SEQUENCE: 9

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Val His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

-continued

```
<210> SEQ ID NO 10
<211> LENGTH: 537
<212> TYPE: DNA
<213> ORGANISM: Pan troglodytes

<400> SEQUENCE: 10
atgcacagct cagcactgct ctgttgcctg gtcctcctga ctggggtgag ggccagccca      60
ggccagggca cccagtctga aacagctgc  acccacttcc caggcaacct gcctaacatg     120
cttcgagatc tccgagatgc cttcagcaga gtgaagactt tctttcaaat gaaggatcag     180
ctggacaact tgctgttaaa ggagtccttg ctggaggact ttaagggtta cctgggttgc     240
caagccttgt ctgagatgat ccagttttac ctggaggagg tgatgcccca agctgagaac     300
caagacccag acatcaaggt gcatgtgaac tccctggggg agaacctgaa gaccctcagg     360
ctgaggctac ggcgctgtca tcgatttctt ccctgtgaaa acaagagcaa ggccgtggag     420
caggtgaaga atgcctttaa taagctccaa gagaaaggca tctacaaagc catgagtgag     480
tttgacatct tcatcaacta catagaagcc tacatgacaa tgaagatacg aaactga       537

<210> SEQ ID NO 11
<211> LENGTH: 178
<212> TYPE: PRT
<213> ORGANISM: Bos taurus

<400> SEQUENCE: 11

Met His Ser Ser Ala Leu Leu Cys Cys Leu Val Phe Leu Ala Gly Val
1               5                   10                  15

Ala Ala Ser Arg Asp Ala Ser Thr Leu Ser Asp Ser Ser Cys Ile His
            20                  25                  30

Leu Pro Thr Ser Leu Pro His Met Leu Arg Glu Leu Arg Ala Ala Phe
        35                  40                  45

Gly Glu Ala Lys Thr Phe Phe Gln Met Lys Asp Gln Leu His Ser Leu
    50                  55                  60

Leu Leu Thr Gln Ser Leu Leu Asp Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn His Gly Pro Asp Ile Lys Glu His Val Asn Ser Leu
            100                 105                 110

Gly Glu Lys Leu Lys Thr Leu Arg Leu Arg Leu Arg Arg Cys His Arg
        115                 120                 125

Phe Leu Pro Cys Glu Asn Lys Ser Lys Ala Val Glu Lys Val Lys Arg
    130                 135                 140

Val Phe Ser Glu Leu Gln Glu Arg Gly Val Tyr Lys Ala Met Ser Glu
145                 150                 155                 160

Phe Asp Ile Phe Ile Asn Tyr Ile Glu Thr Tyr Met Thr Thr Lys Met
                165                 170                 175

Gln Lys

<210> SEQ ID NO 12
<211> LENGTH: 537
<212> TYPE: DNA
<213> ORGANISM: Bos taurus

<400> SEQUENCE: 12
atgcatagct cagcactact ctgttgcctg gtcttcctgg ctggggtggc agccagccga      60
```

-continued

```
gatgcgagca ccctgtctga cagcagctgt atccacttgc caaccagcct gccccacatg     120
ctgcgggagc tccgagctgc cttcggcgag gcgaagactt tctttcaaat gaaggaccaa     180
ctgcacagct tactgttgac ccagtctctg ctggatgact ttaagggtta cctgggttgc     240
caagccttgt cggaaatgat ccagtttttac ctggaagagg tgatgccaca ggctgagaac     300
cacgggcctg acatcaagga gcacgtgaac tcactggggg agaagctgaa gaccctgcgg     360
ctgcggctgc ggcgctgtca tcgctttctg ccctgcgaaa acaagagcaa ggcggtggag     420
aaggtgaaga gagtcttcag tgagctccaa gagaggggtg tctacaaagc catgagtgag     480
tttgacatct tcatcaacta catagaaacc tacatgacaa cgaagatgca aaagtga        537
```

<210> SEQ ID NO 13
<211> LENGTH: 34
<212> TYPE: DNA
<213> ORGANISM: Artificial
<220> FEATURE:
<223> OTHER INFORMATION: primer

<400> SEQUENCE: 13

```
cgcggatcca tgcctggctc agcactgcta tgct                                 34
```

<210> SEQ ID NO 14
<211> LENGTH: 31
<212> TYPE: DNA
<213> ORGANISM: Artificial
<220> FEATURE:
<223> OTHER INFORMATION: primer

<400> SEQUENCE: 14

```
gaggatcctc ttagcttttc attttgatca t                                    31
```

STEM CELLS FOR TRANSPLANTATION AND MANUFACTURING METHOD THEREFOR

RELATED APPLICATIONS

This application is a continuation application of patent application Ser. No. 15/966,917, filed Apr. 30, 2018, which is a continuation of patent application Ser. No. 14/892,474, filed Nov. 19, 2015, which is a 371 application of International Application No. PCT/JP2014/063448, having an international filing date of May 21, 2014, which claims priority to Japanese Patent Application No. 2013-108408, filed May 22, 2013, contents of which are incorporated herein by reference in their entirety.

REFERENCE TO APPENDIX [CD ROM/SEQUENCE LISTING]

This application is being filed electronically via EFS-Web and includes an electronically submitted Sequence Listing in .txt format. The .txt file contains a sequence listing entitled "15005_8_Seq_Listing_ST25" created on Mar. 16, 2029 and is 16,384 bytes in size. The sequence listing contained in this .txt file is part of the specification and hereby incorporated by reference in its entirety.

TECHNICAL FIELD

The present invention relates to a mesenchymal stem cell for transplantation having a high survival rate and engraftment rate in cell transplantation, a method for producing the mesenchymal stem cells for transplantation, and an agent enhancing post-transplantation mesenchymal stem cell engraftment.

BACKGROUND ART

Mesenchymal stem cells (hereinafter, also abbreviated to "MSCs" in the present specification) are somatic stem cells having the ability to differentiate into cells belonging to the mesenchyme. MSCs are considered as the most realistic platform for cell transplantation therapy at the moment, on the grounds that, for example, these cells are capable of actively growing and thus facilitate securing the number of cells, are less likely to cause rejection at the time of transplantation, and have low ethical barriers. MSCs are expected to be applied to regenerative medicine such as the regeneration of mesenchymal connective tissue (e.g., bones, blood vessels, and cardiac muscle) or the central nervous system.

MSCs also have the advantages that the cells are applicable to inflammation control therapy for inflammatory diseases and are highly effective for autologous transplantation therapy, which introduces a therapeutic gene to patient's own MSCs (Non Patent Literature 1). Since MSCs further have the property of accumulating at a site having inflammation or tissue damage, or immunosuppressing ability, the transplantation of bone marrow-derived MSCs is carried out at the same time with bone marrow transplantation for the purpose of promoting the engraftment of hematopoietic stem cells (Non Patent Literature 2). The immunosuppressive effect of MSCs is presumed to be limited to a local area at which MSCs have accumulated, so as not to cause strong systemic immunosuppression. MSCs are therefore considered to have higher safety than that of immunosuppressants. Thus, their clinical effects are expected.

Hence, clinical trials have been conducted so far on cell transplantation therapy which involves transplanting MSCs to target tissue, or inflammation control therapy for inflammatory diseases such as graft versus host disease using the immunological control functions of MSCs (Non Patent Literatures 3 to 6). The efficacy or safety of MSCs has been established in Canada and New Zealand where MSC drugs have already been approved.

Nonetheless, MSCs present major problems: the cells have an unstable post-transplantation survival rate or engraftment rate and therefore tend to result in graft failure; and their original properties are difficult to maintain over a long period. Hence, the previous autologous transplantation therapy using MSCs has failed to stably express a therapeutic gene.

CITATION LIST

Non Patent Literature

Non Patent Literature 1: Connick et al., 2012, Lancet Neurol. 11 (2): 150-156

Non Patent Literature 2: Carrancio S., et al., 2012, Cell Transplant., 22: 1171-1183

Non Patent Literature 3: M von Bonin et al., 2009, Bone Marrow Transplant., 43: 245-251

Non Patent Literature 4: Tolar et al., 2011, Hum. Gene Ther., 22: 257-262

Non Patent Literature 5: Si Y. L., et al., 2011, Ageing Res. Rev., 10: 93-103

Non Patent Literature 6: Wang et al., 2012, J. Hematol. Oncol., 5: 19

SUMMARY OF INVENTION

Technical Problem

In light of the problems mentioned above, an object of the present invention is to develop and provide MSCs that have an improved post-transplantation cell survival rate and engraftment rate and are highly safe with fewer adverse reactions, and to provide a method for conveniently producing a stem cell for transplantation having a high cell survival rate and engraftment rate.

Solution to Problem

In order to attain the object, the present inventor has carried out various treatments to MSCs and consequently found that when an anti-inflammatory cytokine interleukin-10 (hereinafter, also abbreviated to "IL-10" in the present specification) is overexpressed in MSCs, the post-transplantation survival rate and engraftment rate of the MSCs are drastically improved.

It has been further found that acquired immunological tolerance can be induced by treating a recipient individual that undergoes cell transplantation or tissue transplantation, with MSCs together with an immunogen at least once before the transplantation.

The present invention is based on these findings and provides the following:

(1) A stem cell for transplantation comprising an MSC capable of overexpressing IL-10.

(2) The stem cell for transplantation according to (1), wherein the overexpression of IL-10 is caused by an exogenous IL-10 expression system.

(3) The stem cell for transplantation according to (2), wherein the IL-10 expression system is a plasmid vector or a virus vector.

(4) The stem cell for transplantation according to any of (1) to (3), wherein the stem cell is intended for the regeneration of mesenchymal connective tissue, the central nervous system, or the liver.

(5) A method for producing a stem cell for transplantation, comprising the step of introducing an IL-10 expression system capable of overexpressing IL-10 to an MSC.

(6) The method for producing a stem cell using transplantation according to (5), wherein the IL-10 expression system is a plasmid vector or a virus vector.

(7) An agent for enhancing engraftment of mesenchymal stem cell, comprising an IL-10 expression system capable of overexpressing IL-10 as an active ingredient.

(8) The agent for enhancing engraftment of mesenchymal stem cell according to (7), wherein the IL-10 expression system is a plasmid vector or a virus vector.

(9) A method for inducing acquired immunological tolerance, comprising: a first step of administering, within a period from 2 to 14 days before introduction of an immunogen, an MSC and an immunogen having the same immunogenicity as that of said immunogen or a part thereof to a recipient individual at least once; and a second step of administering MSCs to the recipient individual on the day before or the very day of the introduction of the immunogen.

(10) The method according to (9), wherein the MSC is a stem cell for transplantation according to any of (1) to (4).

(11) The method according to (9) or (10), wherein the immunogen is a virus, a cell, a tissue, or an organ.

The present specification encompasses the contents described in the specification and/or drawings of Japanese Patent Application No. 2013-108408 on which the priority of the present application is based.

Advantageous Effects of Invention

According to the stem cell for transplantation of the present invention, MSCs that have a high post-transplantation cell survival rate and engraftment rate and are highly safe can be provided.

According to the method for producing a stem cell for transplantation of the present invention, a stem cell for transplantation having a high post-transplantation engraftment rate can be conveniently produced.

According to the agent for enhancing of MSC of the present invention, the post-transplantation cell survival rate and engraftment rate of MSCs can be enhanced.

According to the method for inducing immunological tolerance of the present invention using MSCs, the post-transplantation rejection of cells can be suppressed. Also, the post-transplantation cell survival rate and engraftment rate can thereby be further enhanced.

DESCRIPTION OF DRAWINGS

FIG. 1A shows the in vivo images of the mouse taken 2 and 4 days after the administration. MSCs and recombinant IL-10 (indicated by (+)) were administered to the left lower leg of the mouse, and only MSCs (indicated by (–)) were administered to the right lower leg of the mouse. FIGS. 1B and 1C show quantitative values 2 days and 4 days post-administration, respectively, calculated on the basis of the images of FIG. 1A.

FIG. 2A shows the in vivo image taken 9 days after the administration. The IL-10 expression AAV vector (IL-10) was administered to the left lower leg of the mouse, and the LacZ expression AAV vector (LacZ) was administered to the right lower leg of the mouse. FIG. 2B shows a quantitative value calculated on the basis of the image of FIG. 2A.

FIGS. 3A-C show the survival rate of MSCs after MSCs introducing an IL-10 expression plasmid DNA or a control GFP expression plasmid DNA were administered by local injection to the lower leg of each NOD/Scid mouse. In this drawing, the MSCs transfected with IL-10 expression plasmid DNA (IL-10(+)) was administered to the left lower leg of the mouse, and the MSCs transfected with GFP expression plasmid DNA (IL-10(–)) was administered to the right lower leg of the mouse. FIG. 3A shows the in vivo images of the mouse taken 3 days, 7 days, and 10 days after the administration (0 day). FIG. 3B shows an IL-10 expression level in MSCs after culture for 12 days from the transfection of the IL-10 expression plasmid DNA or the GFP expression plasmid DNA. FIG. 3C shows quantitative values 3 days, 7 days, 10 days, and 12 days post-administration calculated on the basis of the images of FIG. 3A.

FIG. 5A shows results about MSCs 7 days after the gene transfection with a GFP expression AAV vector (AAV1-GFP). The arrows represent MSCs expressing GFP by the transduction of the GFP expression AAV vector. FIG. 5B shows results about the expression of IL-10 in MSCs 7 days after the transduction of AAV1-GFP or a mouse IL-10 expression AAV vector (AAV1-IL-10).

FIG. 6A shows the in vivo images of the mouse the indicated numbers of days after the administration of MSCs. In this drawing, vIL-10(+)MSCs, which are MSCs transducing AAV1-IL-10, were administered to the left lower leg of the mouse (IL-10(+)), and vIL-10(–)MSCs, which are MSCs transducing control AAV1-GFP, were administered to the right lower leg of the mouse (IL-10(–)). FIG. 6B shows quantitative values (n=5) calculated on the basis of the results of FIG. 6A.

FIG. 7A shows the image of the engraftment of vIL-10(–)MSCs in the muscular tissue. FIG. 7B shows the image of the engraftment of vIL-10(+)MSCs in the muscular tissue. FIG. 7C shows the engraftment rates of vIL-10(−)MSCs and vIL-10(+)MSCs calculated from the images of histological staining.

FIG. 11A is the pathologic image of MSCs in muscular tissue. The sites indicated by arrows encircled by broken lines represent the engraftment of transplanted vIL-10(+)MSCs at inflammation sites. The sites indicated by arrowheads represent myofibers newly formed from the engrafted MSCs. In FIG. 11B, the bright cells encircled by a broken line represent that MSCs were fused with myoblasts in vitro.

FIG. 12A shows a control dog (Cont-AAV) in which only an immunogen AAV9-Luc was locally administered to the tibialis anterior muscle tissue of a normal dog without the immunological tolerance induction treatment of the present invention. FIG. 12B shows an immunological tolerance-induced dog (MSCs+AAV) in which MSCs were locally administered together with the immunogen AAV9-Luc to the same site of a normal dog as above on the basis of the method for inducing acquired immunological tolerance of the present invention. FIG. 12C shows a control dog (Cont-MSCs) in which only MSCs were locally administered to the same site of a normal dog as above without the administration of the immunogen AAV9-Luc. The left diagrams of FIGS. 12A to 12C show a timetable for the experiment for each dog. i.v. denotes intravenous administration, and i.m. denotes intramuscular administration (local administration). The right diagrams thereof show that the tibialis anterior muscle tissue was biopsied, and the expression of a marker gene of luciferase derived from the immunogen AAV9 was detected using an anti-luciferase antibody. In the diagrams, the luciferase-expressing cells are indicated as bright cells. In the diagrams, the scale bar is 100 μm.

FIG. 13A shows a control dog (Cont-AAV) in which only an immunogen AAV9-Luc was intravenously injected to a normal dog without the immunological tolerance induction treatment of the present invention. FIG. 13B shows an immunological tolerance-induced dog (MSCs+AAV) in which MSCs were intravenously injected together with the immunogen AAV9-Luc to a normal dog on the basis of the method for inducing acquired immunological tolerance of the present invention.

FIG. 13C shows an immunological tolerance-induced dog (DMD/MSCs+AAV) in which MSCs were intravenously injected together with an immunogen AAV9-μDys to a muscular dystrophy-affected dog (DMD) on the basis of the method for inducing acquired immunological tolerance of the present invention. The left diagrams of FIGS. 13A to 13C show the timetable for the experiment for each dog. i.v. denotes intravenous administration. The right diagrams thereof show that the temporal muscle was biopsied, and the expression of luciferase was detected using an anti-luciferase antibody (FIGS. 13A and 13B) or the expression of microdystrophin was detected using an anti-dystrophin antibody (FIG. 13C). The white spots seen in each diagram are nuclei. In the diagrams, the luciferase- or microdystrophin-expressing cells are indicated as bright cells. In the diagrams, the scale bar is 100 μm (FIGS. 13A and 13B) and 50 μm (FIG. 13C).

DESCRIPTION OF EMBODIMENTS

1. Stem Cell for Transplantation

1-1. Summary and Definition

Figures 1A, 1B, 1C:
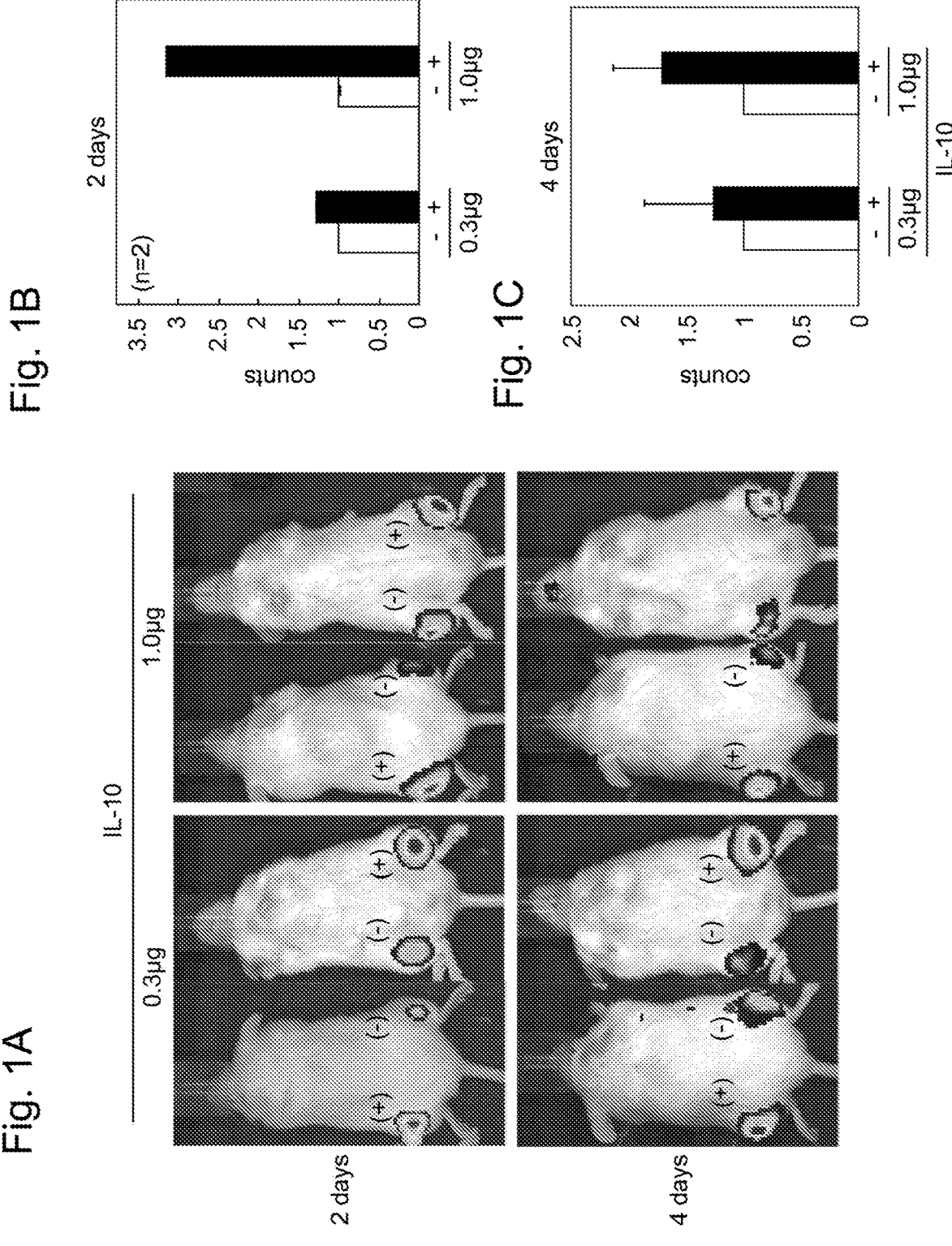
FIGS. 1A-C show the survival rate of MSCs after recombinant IL-10 was administered by local injection together with MSCs to the lower leg of each NOD/Scid mouse.

The first aspect of the present invention provides a stem cell for transplantation.

The "stem cell for transplantation" refers to a stem cell intended for cell transplantation and is aimed at being transplanted to a particular tissue of a recipient individual (or a recipient) and engrafted at the transplantation site and/or neighboring sites thereof so that the cell is allowed to differentiate properly in response to the ambient environment. The stem cell for transplantation of this aspect can be preferably used, particularly, in tissue regeneration such as the replacement or regeneration of mesenchymal connective tissue (e.g., bones, blood vessels, and cardiac muscle), the central nervous system, or liver tissue. In the present specification, the "recipient individual" is a vertebrate, preferably a bird or a mammal (including a human, a dog, a cat, a rabbit, a pig, cattle, sheep, a goat, a horse, a monkey, and a rodent), more preferably a human.

The "engraftment" generally means that a transplanted cell, tissue, or organ becomes capable of exerting its original functions at the transplantation site. In the present specification, an object to be transplanted is a stem cell. In this respect, the engraftment means that, particularly, a transplanted stem cell has the functions of timely expressing a predetermined gene at the transplantation site or neighboring sites thereof, etc., and differentiating properly in response to the ambient environment. The "engraftment rate" described in the present specification refers to the ratio of engrafted stem cells to transplanted stem cells. On the other hand, the "survival rate" described in the present specification refers to the ratio of stem cells surviving after transplantation to transplanted stem cells. The engraftment rate or the survival rate may be calculated from an absolute value such as the number of cells or may be calculated from a relative value such as cell-derived label intensity.

1-2. Constitution

The stem cell for transplantation of the present invention comprises a mesenchymal stem cell capable of intracellularly overexpressing interleukin-10.

The "mesenchymal stem cells (MSCs)" are, as mentioned above, cells having the ability to differentiate into cells belonging to the mesenchyme, such as osteoblasts, adipocytes, myocytes, and chondrocytes. MSCs are also known to have the ability to differentiate plastically into nerve cells (ectoderm-derived) or hepatic cells (endoderm-derived), across germ layers. The stem cell for transplantation of this aspect is based on an MSC.

The "interleukin-10 (IL-10)" is an anti-inflammatory cytokine. IL-10 is produced in many cells including type 2 helper T cells (Th2 cells) as well as monocytes, macrophages, mast cells, activated B cells, and keratinocytes, and is known to suppressively control the functions of macrophages in addition to suppressing inflammatory symptoms by suppressively controlling inflammatory cytokine production or the like through its action on monocyte lineage cells.

In the present specification, the IL-10 encompasses wild-type IL-10 as well as variant-type IL-10 and IL-10 fragments that maintain biological activity equivalent to or higher than that of wild-type IL-10.

In the present specification, the "wild-type IL-10" refers to the IL-10 protein of each organism species that is encoded by the most abundant allele among naturally occurring allele groups and has the original functions of IL-10. The wild-type IL-10 corresponds to, for example, human IL-10 shown in SEQ ID NO: 1, mouse IL-10 shown in SEQ ID NO: 3, rat IL-10 shown in SEQ ID NO: 5, dog IL-10 shown in SEQ ID NO: 7, chimpanzee IL-10 shown in SEQ ID NO: 9, and bovine IL-10 shown in SEQ ID NO: 11.

In the present specification, the "variant-type IL-10" refers to an IL-10 protein having a variation in the wild-type IL-10. Specifically, the variant-type IL-10 means a variant containing the deletion, substitution, or addition of one or several amino acids in the amino acid sequence of wild-type IL-10, or a variant having 85% or more or 90% or more, preferably 95% or more, 97% or more, 98% or more, or 99% or more amino acid identity to the amino acid sequence. In this context, the term "several" refers to 2 to 10, 2 to 7, 2 to 5, 2 to 4, or 2 or 3. The % "identity" refers to the ratio of identical amino acids of an amino acid sequence of interest to the total number of amino acids of wild-type IL-10 when the amino acid sequence of wild-type IL-10 and the amino acid sequence of interest are aligned such that the maximum degree of identity is achieved with or without optionally introduced gaps using a protein search system based on BLAST or FASTA.

In the present specification, the "IL-10 fragment" refers to a polypeptide fragment of the wild-type IL-10 or the variant-type IL-10. The length and region of amino acids of the IL-10 fragment are not particularly limited as long as the length and region allow the biological activity of the wild-type IL-10 to be maintained. Usually, a polypeptide fragment containing the functional domain of IL-10 without disruption is preferably used. In this context, the functional domain refers to a region that is responsible for suppressive activity and functions specific for IL-10 or is essential for exerting the functions.

MSCs have an endogenous IL-10 gene encoding IL-10 and are capable of expressing IL-10 attributed to the gene. Hence, a feature of the stem cell for transplantation of this aspect is that the stem cell overexpresses IL-10 more than normal MSCs. In the present specification, the phrase "overexpressing IL-10" refers to an expression level 2 times or more, preferably 5 times or more, more preferably 10 times or more, further preferably 20 times or more the expression level of IL-10 in normal MSCs.

The mechanism under which the stem cell for transplantation of this aspect overexpresses IL-10 is not particularly limited. For example, the overexpression may be based on the enhanced expression of endogenous IL-10 or may be based on an exogenous IL-10 expression system.

The "enhanced expression of endogenous IL-10" is not particularly limited by its mechanism as long as the expression level of the IL-10 gene on the genomes of MSCs is eventually enhanced. Examples of MSCs having such enhanced expression of endogenous IL-10 include variant-type MSCs allowed to overexpress IL-10 due to a variation in an enhancer or a promoter controlling the expression of the IL-10 gene, and variant-type MSCs having, on their genomes, multicopy IL-10 genes resulting from duplication.

The "exogenous IL-10 expression system" refers to a foreign IL-10 expression system introduced in MSCs.

The "IL-10 expression system" refers to one expression unit containing the IL-10 gene in an expressible state in MSCs. An expression unit that permits persistent expression of the IL-10 gene is preferred.

The "IL-10 gene" refers to a gene encoding the IL-10, or a fragment thereof. The IL-10 gene corresponds to, for example, a human IL-10 gene shown in SEQ ID NO: 2 encoding the human IL-10 shown in SEQ ID NO: 1, a mouse IL-10 gene shown in SEQ ID NO: 4 encoding the mouse IL-10 shown in SEQ ID NO: 3, a rat IL-10 gene shown in SEQ ID NO: 6 encoding the rat IL-10 shown in SEQ ID NO: 5, a dog IL-10 gene shown in SEQ ID NO: 8 encoding the dog IL-10 shown in SEQ ID NO: 7, a chimpanzee IL-10 gene shown in SEQ ID NO: 10 encoding the chimpanzee IL-10 shown in SEQ ID NO: 9, and a bovine IL-10 gene shown in SEQ ID NO: 12 encoding the bovine IL-10 shown in SEQ ID NO: 11.

The IL-10 expression system has the IL-10 gene as well as constituents necessary for expressing the IL-10 gene in MSCs. Such constituents include, for example, a promoter and a terminator. In the IL-10 expression system, the IL-10 gene is located in an expressible state under the control of the promoter and the terminator in a nucleic acid expression system. The IL-10 expression system may additionally contain an enhancer, a poly-A addition signal, a 5'-UTR (untranslated region) sequence, a tag or selective marker gene, a multicloning site, a replication origin, and the like.

The promoter is not particularly limited as long as the promoter is operable in MSCs. For example, when MSCs containing the IL-10 expression system are derived from a mammal, a promoter of a virus (e.g., human cytomegalovirus, retrovirus, polyomavirus, adenovirus, and simian virus 40 (SV40)) or a mammalian cell-derived promoter such as elongation factor 1a (EF1α) can be used, which is a promoter operable in a mammal. Promoters are known to be classified according to their expression control properties into an overexpression-type promoter, a constitutive promoter, a site-specific promoter, a stage-specific promoter, or an inducible promoter, etc. The promoter for use in the IL-10 expression system is preferably an overexpression-type promoter or a constitutive promoter. It is desirable that, even if the expression of the endogenous IL-10 gene in transplanted stem cells is positionally or quantitatively controlled at the transplantation site, the IL-10 expression system should be capable of constantly expressing the IL-10 gene independently from the control. In the IL-10 expression system, the promoter is positioned upstream from the start codon of the IL-10 gene.

The terminator is not particularly limited as long as its sequence can terminate the transcription of the IL-10 gene transcribed by the promoter in MSCs. In the IL-10 expression system, the terminator is positioned downstream from the stop codon of the IL-10 gene.

The IL-10 expression system includes an expression system prepared by isolating one expression unit necessary for expressing the IL-10 gene, as it is from the genome and incorporating the expression unit therein, and an expression system artificially constructed by combining a recombinant IL-10 gene with each constituent. In the present invention, any nucleic acid expression system can be used. The IL-10 expression system may be a monocistronic system containing one IL-10 gene in one system or may be a polycistronic system containing two or more IL-10 genes in one system.

Examples of the IL-10 expression system include an IL-10 expression-type plasmid vector, an IL-10 expression-type virus vector, and an IL-10 expression-type artificial chromosome vector. A virus vector is preferred.

The "plasmid vector" refers to a gene vector modified from a plasmid. The plasmid moiety for use in the IL-10 expression-type plasmid vector is not particularly limited as long as the IL-10 gene can be expressed in MSCs. The plasmid vector lacks the ability to self-renew in MSCs. In the case of using the plasmid vector, the expression of the IL-10 gene is therefore usually transient unless the plasmid vector is inserted into the genomes of MSCs. A commercially available expression plasmid, for example, an expression plasmid for mammal cells, may be used as the plasmid moiety serving as the backbone of the IL-10 expression system.

The "virus vector" refers to a gene vector that exploits the infectious ability or the ability to replicate of a virus. The virus vector is constituted by a virus particle containing a virus nucleic acid (including DNA or RNA) in which a foreign gene (here, the IL-10 gene) is incorporated after removal of genes related to pathogenicity from the virus genome. In the IL-10 expression system, a vector derived from any virus known in the art can be used. Examples thereof include retrovirus (including lentivirus and mouse Moloney leukemia virus), adenovirus, adeno-associated virus (hereinafter, referred to as "AAV"), and Sendai virus. AAV, which is a nonpathogenic virus belonging to the parvovirus, cannot grow autonomously due to deficiency in the ability to self-renew and is low infective because its growth requires the coinfection of adenovirus or Herpes virus. This virus is also low immunogenic in hosts. Hence, the virus has the advantage that it is highly safe as a gene vector. AAV has a wide host range and is capable of infecting various cells such as myocytes, nerve cells, and hepatic cells. Thus, AAV is also preferred as a virus vector for the IL-10 expression system according to this aspect. The virus vector can be prepared as a virus particle that is contained in a coat protein composed of a capsid or a coated particle and has the ability to infect cells.

The "artificial chromosome" includes human artificial chromosome (HAC).

The stem cell for transplantation of this aspect can contain a plurality of identical or different IL-10 expression systems in one MSC. This increases the number of IL-10 expression systems per cell, thereby increasing an IL-10 expression level per MSC to attain an overexpression state, even if the expression level of IL-10 from each individual system is low.

1-3. Effect

According to the stem cell for transplantation of this aspect, stem cells having a high post-transplantation cell survival rate and engraftment rate and fewer adverse reactions can be provided. Accordingly, the stem cell for transplantation of this aspect is transplanted in mesenchymal connective tissue (e.g., bones, blood vessels, and cardiac muscle), the central nervous system, or the liver so that this transplanted cell is engrafted in the transplantation tissue and induced to differentiate appropriately in response to the ambient environment. The stem cell for transplantation of this aspect can therefore be applied to regenerative medicine such as tissue regeneration.

2. Method for Producing Stem Cell for Transplantation

2-1. Summary

The second aspect of the present invention provides a method for producing a stem cell for transplantation. A feature of the production method of this aspect is that an IL-10 expression system is introduced to MSCs to produce MSCs capable of overexpressing IL-10.

2-2. Method

The production method of this aspect comprises an IL-10 expression system introduction step. The IL-10 expression system introduction step refers to the step of introducing at least one IL-10 expression system capable of overexpressing IL-10 to an MSC.

The constitution of the IL-10 expression system used in the IL-10 expression system introduction step may be the same as that of the IL-10 expression system described in the first aspect.

The IL-10 expression system can be prepared according to a method known in the art, for example, a method described in Green & Sambrook, Molecular Cloning, 2012, Fourth Ed., Cold Spring Harbor Laboratory Press.

Hereinafter, the preparation of a plasmid vector or a virus vector as the IL-10 expression system will be described with reference to specific examples. However, the preparation of the IL-10 expression system is not limited to the following.

(1) Preparation of Plasmid Vector

IL-10 gene cloning is carried out. The species from which the IL-10 gene used is derived is not particularly limited as long as activity as IL-10 is possessed in MSCs to which the IL-10 expression system is introduced. An IL-10 gene derived from the same organism species as that of MSCs for introduction is preferred. For example, in the case of introducing the IL-10 expression system to human-derived MSCs, the IL-10 gene is preferably the human IL-10 gene shown in SEQ ID NO: 2. The IL-10 gene cloning can be carried out according to a method known in the art, for example, a method described in Green & Sambrook (2012) (idem). For example, in the case of cloning the human IL-10 gene, an appropriate region is selected from the nucleotide sequence represented by SEQ ID NO: 2, and an oligonucleotide having this nucleotide sequence is chemically synthesized. The chemical synthesis can exploit the commissioned synthesis service of a life science manufacturer. Next, the human IL-10 gene is isolated from a human cDNA library with the oligonucleotide as a probe on the basis of a method known in the art, for example, a plaque hybridization method. For the detailed gene isolation method, see, for example, Green & Sambrook (2012) (idem). The human cDNA library is commercially available from each life science manufacture, and such a commercially available product may therefore be used. Alternatively, oligonucleotides serving as a primer pair may be chemically synthesized on the basis of the nucleotide sequence represented by SEQ ID NO: 2, and the human IL-10 gene of interest can be amplified by a nucleic acid amplification method such as PCR using the primer pair and a human genomic DNA or cDNA library as a template. For the nucleic acid amplification, DNA polymerase, such as pfu polymerase, which has 3'-5' exonuclease activity and has high fidelity, is preferably used. The detailed conditions for the nucleic acid amplification, see, for example, a method described in Innis M. et al. (Ed.), 1990, Academic Press, PCR Protocols: A Guide to Methods and Applications. The isolated human IL-10 gene is inserted, if necessary, to an appropriate plasmid and cloned in a microbe such as *E. coli*. Then, the full-length nucleotide sequence is confirmed on the basis of a known technique. In addition, a human IL-10 cDNA clone is commercially available and may therefore be purchased for use.

Subsequently, the cloned human IL-10 gene is integrated into a predetermined site of a plasmid vector for expression. These series of gene manipulation techniques are techniques well known in the art. For the detailed method, see, for example, Green & Sambrook (2012) (idem).

(2) Preparation of Virus Vector

The basic operation can follow the method for the plasmid vector mentioned above. First, the virus genome is prepared by a method known in the art and then inserted to an appropriate cloning vector (e.g., *E. coli*-derived pBI series, pPZP series, pSMA series, pUC series, pBR series, and pBluescript series) to obtain a recombinant. Next, the IL-10 gene described in the preceding paragraph (1) is inserted to a predetermined site in the virus genome contained in the recombinant, followed by cloning. Subsequently, the virus genome region, which is the IL-10 expression system, can be excised from the recombinant with restriction enzymes. In this way, the virus vector of interest can be obtained.

The method for introducing the IL-10 expression system into MSCs, i.e., the method for transforming MSCs, can employ any appropriate method known in the art.

For example, when the IL-10 expression system is a plasmid vector, a well-known method can be used, such as an electroporation method, a calcium phosphate method, a liposome method, a DEAE dextran method, microinjection, lipofection, or binding with a cell membrane-permeable peptide. For these specific methods, see methods well known in the art, for example, methods described in Green & Sambrook (2012) (idem). Alternatively, the plasmid vector may be introduced to MSCs using a commercially available nucleic acid-introducing agent such as Lipofectamine 2000 (Life Technologies Corporation).

When the IL-10 expression system is a virus vector, the virus vector can be allowed to virally infect MSCs so that the virus vector is transduced into the MSCs. For the infection method, see a method well known in the art, for example, a method described in Green & Sambrook (2012) (idem), depending on the type of the virus used in the vector.

In order to stably and persistently express IL-10 in MSCs, the IL-10 expression system may be inserted into the genomes of MSCs via homologous recombination.

2-3. Effect

According to the production method of this aspect, stem cells for transplantation based on MSCs can be produced conveniently and relatively inexpensively. This method achieves easy obtainment of MSCs having a high post-transplantation engraftment rate.

3. Agent Enhancing Mesenchymal Stem Cell Engraftment

3-1. Summary

The third aspect of the present invention provides an agent for enhancing engraftment of mesenchymal stem cell (agent enhancing MSC engraftment). The agent enhancing MSC engraftment of this aspect is an agent for converting MSCs to stem cells for transplantation having a high cell survival rate and engraftment rate. A feature thereof is to drastically enhance the post-transplantation survival rate and engraftment rate of MSCs.

3-2. Constitution

The agent enhancing MSC engraftment of this aspect comprises an IL-10 expression system capable of overexpressing IL-10 as an active ingredient. This IL-10 expression system has the same constitution as that of the IL-10 expression system described in the first aspect, so that the description thereof is omitted here. The agent enhancing MSC engraftment of this aspect may be in a dried solid state or may be in a liquid state in which the agent has been dissolved in an appropriate buffer. Because the IL-10 expression system serving as an active ingredient is constituted by a nucleic acid, it is preferred that the IL-10 expression system should be stored under conditions free from nuclease and where the IL-10 expression system is stably retained without being degraded by the agent enhancing MSC engraftment, for example, at a subzero temperature.

3-3. Use Method

The agent enhancing MSC engraftment of this aspect can attain its purpose by introducing the IL-10 expression system serving as an active ingredient into MSCs, which are cells to be transplanted. The method for introducing the IL-10 expression system into MSCs differs depending on the type of the IL-10 expression system and can be basically carried out according to the method for introducing the IL-10 expression system into MSCs (Method for transforming MSCs) described in the paragraph "2. Method for producing stem cell for transplantation". The MSCs, which are cells to be transplanted, may not only be wild-type MSCs isolated from an organism and cultured, but may also be variant-type MSCs in which a marker gene such as a luciferase expression vector has been introduced in advance.

3-4. Effect

According to the agent enhancing MSC engraftment of this aspect, MSCs for transplantation having a high cell survival rate and engraftment rate can be easily prepared from normal MSCs.

4. Method for Inducing Acquired Immunological Tolerance

4-1. Summary

The fourth aspect of the present invention provides a method for inducing acquired immunological tolerance. A feature of the method of this aspect is to induce the immunological tolerance of a recipient individual in an acquired manner so that immune response to an immunogen, such as a cell or a tissue, which is introduced into the organism, is suppressed.

4-2. Method

The method of this aspect comprises a first step and a second step as essential steps.
(1) First Step
The "first step" is the step of administering, within a period of the predetermined number of days before introduction of an immunogen, an MSC and the immunogen or a part thereof to a recipient individual.

The "immunogen" in this aspect refers to a substance having immunogenicity with the aim of being introduced into an organism and is mainly a protein. Examples thereof include viruses, cells, tissues, and organs. The immunogen used in this step and the immunogen used in the subsequent second step need only to have immunogenicity different from that of the recipient individual and are not necessarily required to be the same types of immunogens. The phrase "having different immunogenicity" refers to differing in immunogenicity or antigenicity. The phrase "having different immunogenicity" refers to, for example, differing in human leucocyte antigen (HLA) type or virus serotype. In the case of transplanting a tissue derived from a human different from a recipient individual to a human as the recipient individual (recipient person), the transplanted tissue and the recipient person differ in HLA type, which is immunogenicity, from each other.

The term "a part thereof" in this aspect means a moiety of the immunogen having a size that permits local administration or intravascular administration to the recipient individual, when the immunogen to be transplanted has too large a size to be locally administered or intravascularly administered via injection or the like. For example, when the immunogen is a particular tissue, the term "a part thereof" refers to one cell or a mass of several cells constituting the tissue.

The MSC used in this aspect may be a normal MSC or may be the MSC as the stem cell for transplantation capable of overexpressing IL-10 described in the first aspect. In the case of using the stem cell for transplantation as the MSC, only this MSC can be administered in this step.

In this step, the transplantation date of the immunogen to the recipient individual is defined as a reference date (day 0), and the MSC and the immunogen or a part thereof are administered into the recipient individual within a period (13 days) from 2 to 14 days before the reference date, preferably within a period (9 days) from 2 to 10 days before the reference date, more preferably within a period (7 days) from 2 to 8 days before the reference date. The MSC and the immunogen or a part thereof may be administered to the recipient individual at the same time, either after being mixed with each other and infecting the MSC with the immunogen (in the case of a virus) or individually, or may be administered sequentially. In this case, the order of administration is not limited. The immunogen or a part thereof may be administered to the recipient individual after administration of MSCs, or vice versa. The interval of administration between them is within 30 minutes, preferably within 10 minutes.

The number of doses within the aforementioned period can be at least one. Usually, one to several doses suffice. However, the administration is carried out once per day as a rule. The administration timing within the period is not limited. For example, when the number of doses within the period is one, this administration is preferably carried out within a period from 6 to 8 days before the reference date.

The method for administration to the recipient individual is not limited, and a local administration method which involves directly administering the immunogen to an intended transplantation site or the neighborhood thereof, or a systemic administration method mediated by the circulatory system can be preferably used. Examples of the local administration method include subcutaneous administration, intramuscular administration, intraarticular administration, intramedullary administration, administration into tissues (including administration into organs), and intraperitoneal administration. Examples of the systemic administration method mediated by the circulatory system include intravenous administration, intraarterial administration, and intralymphatic administration. Any of these administration methods are preferably based on the administration of a liquid formulation by injection. The administration method based on intravenous injection is an administration method suitable for this aspect.

The number of MSCs and the amount of the immunogen per dose in this step are not limited. The number of MSCs can fall within the range of, for example, $5 \times 10^5$ cells/kg B.W. (Body Weight) to $2 \times 10^6$ cells/kg B.W. The amount of the immunogen differs depending on the type thereof and can fall within the range of $1 \times 10^5$ v.g./cell to $1 \times 10^6$ v.g./cell for a virus or the range of $1 \times 10^2$ to $1 \times 10^{10}$ cells/kg B.W.
(2) Second Step
The "second step" refers to the step of administering an MSC to the recipient individual on the day before or the very day of the introduction of the immunogen.

The MSC to be administered in this step may be an MSC different from that administered in the first step. For example, a normal MSC can be administered in the first step, and the stem cell for transplantation capable of overexpressing IL-10 described in the first aspect can be administered in this step.

The MSC may be administered on any of the day before and the very day of the immunogen introduction date, i.e., the reference date, and is preferably administered on the day before. In the case of administering the MSC on the very day of the reference date, the MSC may be administered separately from the immunogen to be introduced, or may be administered at the same time with the introduction of the immunogen. For the administration separate from the introduction of the immunogen, it is preferred to introduce the immunogen after administration of the MSC. For the administration at the same time with the introduction of the immunogen, the immunogen may be introduced as a mixture with the MSC, provided that the immunogen to be introduced can be locally administered or systemically administered via the circulatory system, as with a virus.

4-3. Effect

In the recipient individual treated by the method for inducing acquired immunological tolerance of this aspect, immunological tolerance is induced against the immunogen used in the pretreatment. Accordingly, the immunogen can then be introduced to the recipient individual by a method known in the art, thereby suppressing immune response to the introduced immunogen in the recipient individual. Hence, when the immunogen is a cell, a tissue, or an organ, rejection caused by immune response in the recipient individual resulting from the transplantation thereof can be suppressed or circumvented. As a result, the post-transplantation survival rate of the cell or the like can be enhanced, and the engraftment rate thereof in the recipient individual can be enhanced.

Comparative Example 1

<Verification of Effect of Improving Survival Rate of MSCs by Recombinant IL-10>
(Objective)

The objective is to verify the effect of improving the survival rate of transplanted cells after recombinant mouse IL-10 was introduced together with MSCs into muscular tissue.
(Method)
1. Cultured Cells and Culture Conditions A luciferase expression vector pLuc was introduced to rat bone marrow-derived MSCs (SD-rat MSCs) to establish a cell line SD-rat MSCs-Luc stably expressing luciferase. SD-rat MSCs-Luc was inoculated to a dish containing a DMED/F-12 (1:1) (GIBCO) medium containing 10% FBS (Nichirei Corp.) and cultured at 37° C. in the presence of 5% $CO_2$. Hereinafter, the "MSCs" described in Comparative Examples 1 and 2 and Examples 1 and 2 in the present specification mean the "SD-rat MSCs-Luc" used in the experiment.
2. Local Transplantation to Mouse The MSCs thus cultured were recovered by trypsin treatment, and the number of cells was adjusted with PBS into $5 \times 10^6$ cells/100 μL to prepare an MSC solution. Recombinant mouse IL-10 (PeproTech, Inc.) was adjusted to 0.3 μg/10 μL saline (hereinafter, abbreviated to "0.3 μg of IL-10") and 1.0 μg/10 μL saline (hereinafter, abbreviated to "1.0 μg of IL-10"), and each solution was mixed with the MSC solution. The resulting mixture was administered by local injection to the left lower leg of each NOD/Scid mouse (3 months old, male) to transplant the MSCs. For a control, an MSC solution free from recombinant mouse IL-10 (IL-10(−)MSCs) was administered by local injection to the right lower leg. 1 and 4 days after the administration, the same amount of recombinant mouse IL-10 as above was additionally administered to the left lower leg.
3. Verification of Survival Rate of Transplanted MSCs 2, 4, and 9 days after the administration, in vivo bioimaging analysis was conducted to measure the luciferase luminescence activity of the transplanted MSCs ex vivo from the mouse. 200 to 300 μL of a 15 mg/mL luciferin solution was intraperitoneally administered at 150 mg/kg to the mouse under 2% isoflurane anesthesia. 20 minutes later, the luciferase luminescence intensity was measured using IVIS® Imaging System (PerkinElmer, Inc.) and digitalized as ROI (region of interest) using software Living Image® 3.2. Then, the survival rate of the transplanted MSCs after the administration was quantitatively analyzed. When the ROI of the control IL-10(−)MSCs was defined as 1, the ratio of the luminescence value of IL-10(+)MSCs was calculated.
(Results)

The results are shown in FIGS. 1A-C. FIG. 1A shows the images of the mouse (n=2) taken 2 and 4 days after the administration. FIG. 1B shows quantitative values calculated on the basis of the images of FIG. 1A. When 0.3 μs of IL-10 was administered together with MSCs, no large difference in survival rate was confirmed as compared with IL-10(−)MSCs, as to both the results 2 days and 4 days post-administration. By contrast, when 1.0 μg of IL-10 was administered together with MSCs, the survival rate was 3.2 times and 1.7 times 2 days and 4 days, respectively, after the administration. These results demonstrated dose-dependent improvement in the survival rate of transplanted MSCs by IL-10.

However, for both 0.3 μg and 1.0 μg of IL-10, the survival of MSCs was unable to be confirmed 9 days after the administration. Thus, it was revealed that, in the case of administering IL-10 together with MSCs into a tissue, the survival rate of the transplanted MSCs can be improved in a manner dependent on the dose of IL-10, though this effect is transient and engraftment is difficult.

Comparative Example 2

<Verification of Effect of Improving Survival Rate of MSCs by Concurrent Administration of IL-10 Expression AAV Vector>
(Objective)

The objective is to verify the effect of improving the survival rate of MSCs after an IL-10 expression AAV vector was administered at the same time with the MSCs into muscular tissue.
(Method)
1. Preparation of Recombinant AAV In this Comparative Example, recombinant AAV1 (rAAV1) was used. The rAAV1 was prepared according to the method of Okada et al. (Okada, T., et al., 2009, Hum. Gene Ther., 20: 1013-1021; and Okada, T., et al., 2005, Hum. Gene Ther., 16: 1212-1218).

For the preparation of the IL-10 expression AAV vector (AAV1-CAG-mIL-10-WPRE(EW); hereinafter, referred to as "AAV1-IL-10"), first, RNA was collected from mouse peripheral blood lymphocytes and then reverse-transcribed into cDNA by RT-PCR. The coding region of mouse IL-10 was amplified as a recombinant mouse IL-10 gene by PCR using the cDNA as a template and a primer set consisting of SEQ ID NO: 13 (Fw: 5'-CGCGGATC-CATGCCTGGCTCAGCACTGCTATGCT-3') and 14 (Rv: 5'-GAGGATCCTCTTAGCTTTTCATTTTGATCAT-3') having a 5'-BamHI tag.

Subsequently, the amplification product was cleaved with BamHI and then integrated into the BamHI site of a pW-CAG-WPRE vector (Okada, T., et al., 2005, Hum. Gene Ther., 16: 1212-1218) to prepare AAV1-IL-10. The AAV1-IL-10 is capable of persistently expressing IL-10 in a tissue that has received it.

On the other hand, a LacZ expression AAV vector (pAAV-LacZ; hereinafter, referred to as AAV1-LacZ) (Agilent Technologies, Inc.) containing LacZ instead of IL-10 was used as a control.
2. Local Transplantation to Mouse and Verification of Survival Rate of MSCs The basic method followed the method described in Comparative Example 1. 4 days before administration, 100 μL of 10 μM cardiotoxin (Sigma-Aldrich Corp.) was administered by local injection to the right and left lower legs of each NOD/Scid mouse (5 months old, male) to induce muscle injury. AAV1-IL-10 and AAV1-LacZ were each adjusted to $5 \times 10^8$ g.c. and $1 \times 10^9$ g.c. and mixed with an MSC solution having $5 \times 10^6$ cells/100 μL. Each mixture was administered by local injection to the left lower leg for AAV1-IL-10 and the right lower leg for AAV1-LacZ, of the mouse. 9 days after the administration, the survival rate of MSCs was quantitatively analyzed by in vivo bioimaging analysis.

(Results)

Figure 2B:
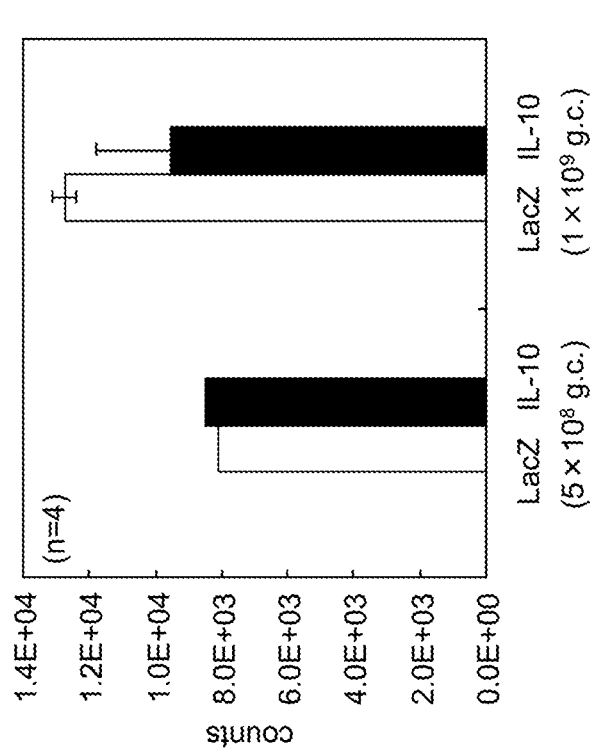
FIGS. 2A-B show the survival rate of MSCs after an IL-10 expression AAV vector and LacZ expression AAV vector as a control were each administered by local injection together with MSCs to the lower leg of each NOD/Scid mouse.
Figure 2A:
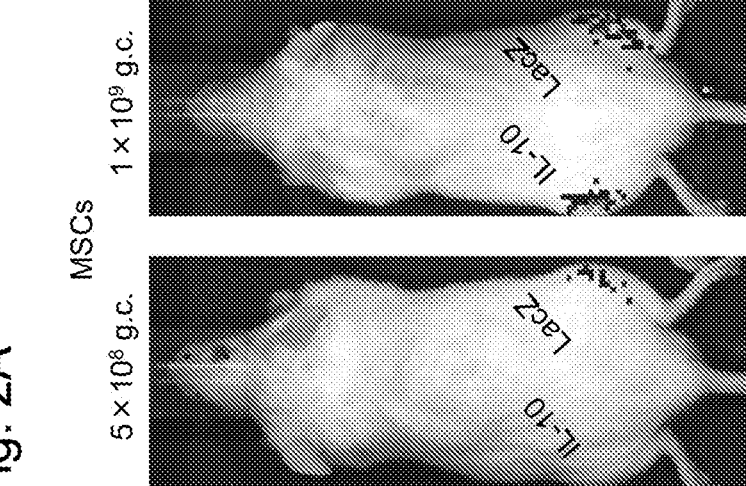

The results are shown in FIGS. 2A-B. FIG. 2A shows the image of the mouse taken 9 days after the administration. FIG. 2B shows a quantitative value (n=4) calculated on the basis of the results of FIG. 2A. Even when AAV1-IL-10 was administered by local injection, the effect of improving the survival rate of the transplanted MSCs was not confirmed, irrespective of the dose. Thus, it was revealed that MSCs cannot be engrafted even if IL-10 is persistently expressed in a tissue that has received it.

Example 1

<Verification of Effect of Improving Survival Rate of MSCs by MSCs Intracellularly Overexpressing IL-10>

(Objective)

The objective is to verify the effect of improving the survival rate of MSCs after the intracellular expression level of IL-10 in MSCs was increased by use of an IL-10 expression plasmid, and an IL-10 concentration in serum.

(Method)

1. Gene Transfection of MSCs with IL-10 Expression Plasmid DNA

2 μg of a mouse IL-10 expression plasmid DNA (pW-CAG-mIL-10-WPRE) or a control GFP expression plasmid DNA (pW-CAG-EGFP-WPRE) was mixed with 100 μL of a Nucleofection solution (Human MSC Nucleofector kit, Lonza Group Ltd.)/$5 \times 10^5$ MSCs, and each mixture was used in gene transfection using an Amaxa Nucleofector system (C-17 mode). The pW-CAG-mIL-10-WPRE was prepared by introducing the recombinant mouse IL-10 gene prepared in Comparative Example 2 to the BamHI site of pW-CAG-WPRE. The pW-CAG-EGFP-WPRE was prepared by introducing an EGFP gene to the BamHI site of pW-CAG-WPRE (Okada, T., et al., 2005, Hum. Gene Ther., 16: 1212-1218). The detailed procedures followed the protocol attached to this product. Hereinafter, the MSCs transfected with the mouse IL-10 expression plasmid DNA are referred to as pIL-10(+)MSCs, and the MSCs introducing the control GFP expression plasmid DNA are referred to as pIL-10(−)MSCs.

2. Verification of Administration by Local Injection to Mouse and Survival Rate

The basic method followed the method described in Comparative Example 1. Immediately after the introduction of each gene to MSCs according to the preceding paragraph "1. Gene transfection of MSCs with IL-10 expression plasmid DNA", a $7.5 \times 10^6$ cells/100 μL pIL-10(+)MSCs solution and a pIL-10(−) MSCs solution were administered by local injection at equal doses to the left lower leg and the right lower leg, respectively, of each NOD/Scid mouse (6 months old, female). 3, 7, 10, and 13 days after the administration, the survival rate of MSCs was quantitatively analyzed by in vivo bioimaging analysis.

3. IL-10 Expression Analysis

For the confirmation of the expression of IL-10 derived from MSCs, a part of the MSCs introducing the gene in the preceding paragraph "1. Gene transfection of MSCs with IL-10 expression plasmid DNA" was inoculated to the aforementioned DMED/F-12 (1:1) medium containing 10% FBS and cultured at 37° C. for 12 days in the presence of 5% $CO_2$, and the resulting culture supernatant was used in ELISA (Mouse IL-10 ELISA Kit, Thermo Fisher Scientific Inc.) according to the attached protocol.

4. Measurement of IL-10 Concentration in Serum 13 days after the administration of MSCs, blood was collected from the heart of the mouse, and the IL-10 concentration in the serum was quantified using Mouse IL-10 ELISA Kit (Thermo Fisher Scientific Inc.). As a control, blood was similarly collected from the mouse in which AAV1-IL-10 was administered by local injection to the MSC transplantation site in Comparative Example 2, and the IL-10 concentration in serum was quantified using this kit.

(Results)

Figures 3A, 3B, 3C:
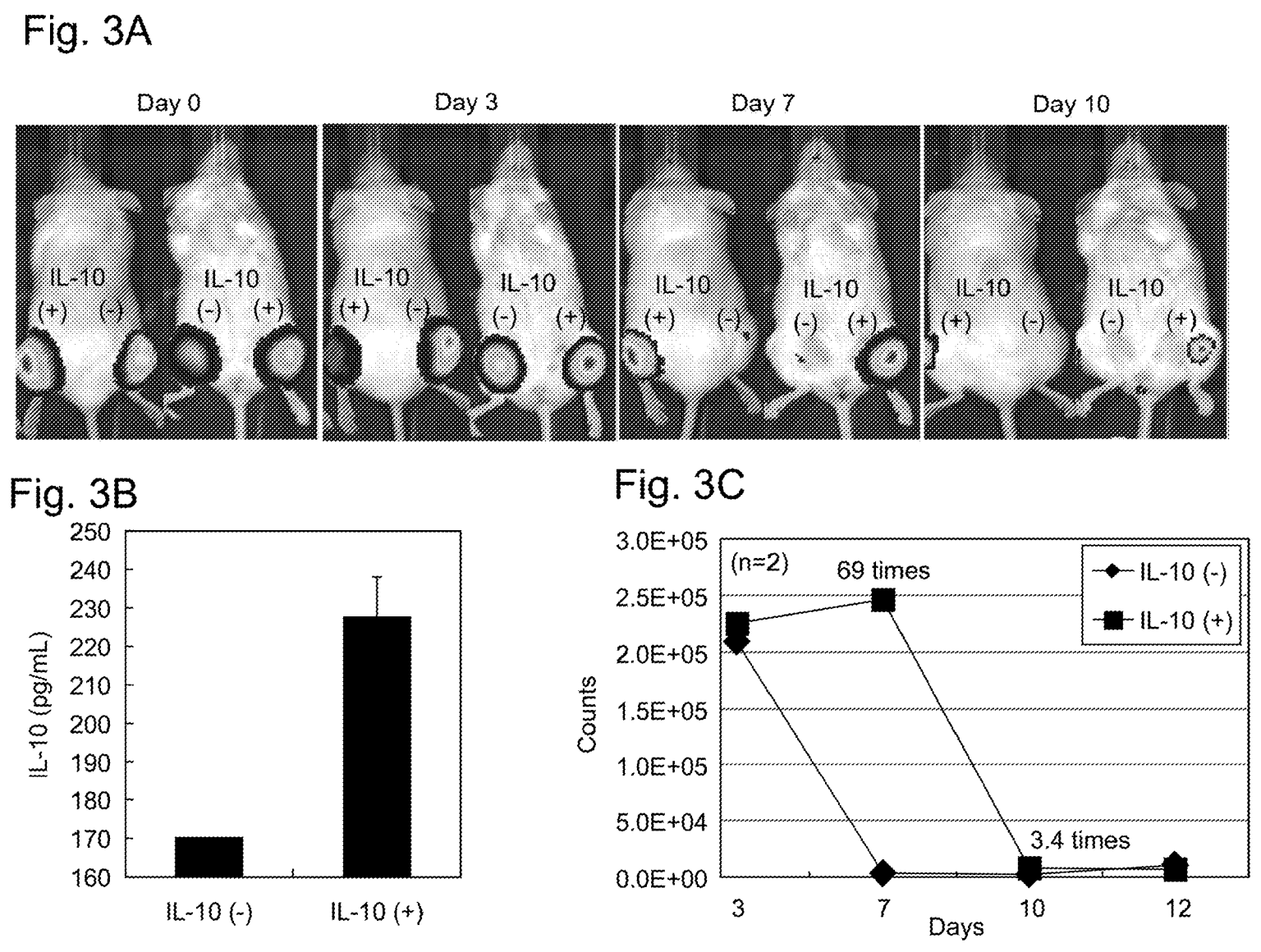

The results are shown in FIGS. 3A-C. FIG. 3A shows the images of the mouse taken the indicated numbers of days after the administration of MSCs. FIG. 3B shows quantitative values (n=2) calculated on the basis of the results of FIG. 3A. FIG. 3C shows the expression level of IL-10 derived from MSCs. pIL-10(+)MSCs exhibited values as high as 69 times and 3.4 times 7 days and 10 days, respectively, after the administration as compared with pIL-10(−)MSCs. By contrast, the signal intensity of luciferase was unable to be confirmed 12 days after the administration. These results suggested that the overexpression of IL-10 in MSCs improves the post-transplantation survival rate of the MSCs and thereby permits engraftment of the MSCs even 10 days after the administration, which is difficult to achieve by conventional methods.

Figure 4:
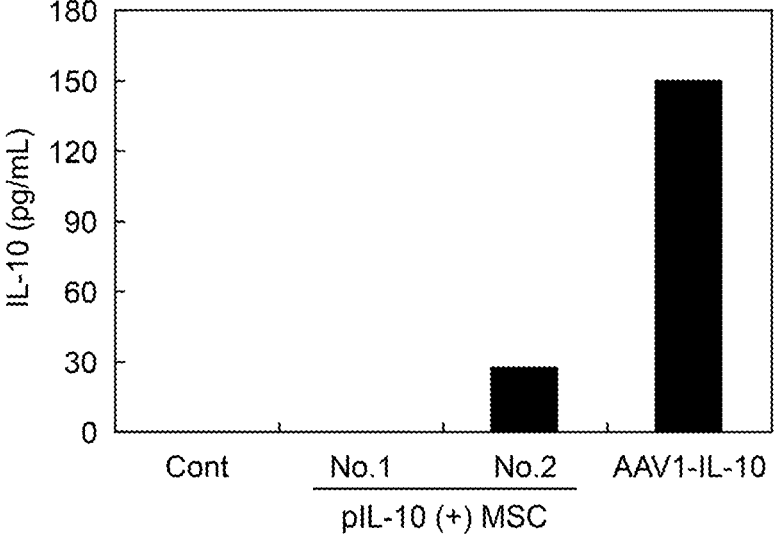
FIG. 4 shows an IL-10 concentration in the serum of each MSC-transplanted mouse. Cont represents a control mouse in which only MSCs were transplanted. pIL-10(+)MSCs represents two mice (No. 1 and No. 2) in which IL-10(+) MSCs, which are the MSCs introducing a mouse IL-10 expression plasmid DNA described in FIG. 3A, were transplanted. AAV1-IL-10 represents a mouse in which a mouse IL-10 expression AAV vector AAV1-IL-10 was administered together with MSCs to transplantation site.

FIG. 4 shows the IL-10 concentration in the serum of the MSC-transplanted mouse. The mouse in which AAV1-IL-10 was administered by local injection to the MSC transplantation site in Comparative Example 2 had a mild rise in the IL-10 concentration (up to 150 pg/mL) in serum. By contrast, two mice (No. 1 and No. 2) of this Example in which pIL-10(+)MSCs intracellularly expressing IL-10 were transplanted had only a slight rise in IL-10 concentration in serum. In general, an elevated IL-10 concentration in serum causes adverse effects such as hematopoietic injury or reduction in immunity. Thus, it was demonstrated that the transplantation of MSCs intracellularly overexpressing IL-10 causes fewer adverse reactions resulting from an IL-10 concentration in serum and has high safety.

Example 2

<Verification of Effect of Improving Survival Rate and Engraftment Rate by MSCs Overexpressing IL-10>

(Objective)

The objective is to verify the effect of improving the survival rate and engraftment rate of MSCs after the intracellular expression level of IL-10 in the MSCs was increased by use of an IL-10 expression AAV vector.

(Method)

1. Gene Transfection of MSCs with AAV Vector and Confirmation of Expression

The recombinant AAV was prepared according to the method described in Comparative Example 2. SD-rat MSCs-Luc was inoculated at $1 \times 10^5$ cells/well to a 24 well-plate (IWAKI/AGC Techno Glass Co., Ltd.) containing a DMED/F-12 (1:1) medium containing 10% FBS. After cell adhesion, an unpurified culture supernatant containing the mouse IL-10 expression AAV vector AAV1-IL-10 or a GFP expression AAV vector AAV1-CAG-EGFP-WPRE(EW) (hereinafter, referred to as "AAV1-GFP") at $5.0 \times 10^{10}$ g.c. was added thereto for the gene transfection of the SD-rat MSCs. After overnight culture at 37° C. in the presence of 5% $CO_2$, the medium was replaced with a fresh one every 2 days, and the culture solution was recovered for 2 days from 5 to 7 days after the gene transduction. 7 days after the gene transfection, GFP-expressing cells were observed under a fluorescence microscope (Olympus Corp., IX71) to determine gene transduction efficiency. The IL-10 expression level in the recovered culture supernatant was quantified by ELISA (Mouse IL-10 ELISA Kit, Thermo Fisher Scientific Inc.). The AAV1-GFP was prepared by inserting the EGFP gene prepared in Example 1 to the BamHI site of AAV1-CAG-WPRE(EW).

2. Administration by Local Injection to Mouse and Verification of Survival Rate and Engraftment Rate The basic method followed the method described in Comparative Example 1. Similarly to the preceding paragraph "1. Gene transduction of MSCs with AAV vector and confirmation of expression", the gene transduction of MSCs was carried out using an unpurified culture supernatant containing the AAV1-IL-10 or the control AAV1-GFP. A DMED/F-12 (1:1) medium containing 10% FBS supplemented with each AAV vector at $6.0 \times 10^{12}$ g.c. was placed in a T225 flask (Thermo Fisher Scientific Inc.) to which $1.6 \times 10^7$ cells of MSCs adhered. After culture at $37^\circ$ C. for 5 days in the presence of 5% $CO_2$, each AAV vector was added again at $1.1 \times 10^{13}$ g.c./flask, and the culture was continued for 2 days for gene transduction. Hereinafter, the MSCs transducing the AAV1-IL-10, which correspond to the stem cell for transplantation of the present invention, are referred to as "vIL-10(+)MSCs", and the MSCs transducing the control AAV1-GFP are referred to as "vIL-10(-)MSCs". After the gene transfection, the MSCs ($1.0 \times 10^7$ cells) were administered by local injection to the left lower leg (vIL-10(+)MSCs) and the right lower leg (vIL-10(-)MSCs) of each NOD/Scid mouse (3 months old, 5 females and 1 male). 3, 7, 18, 27, 31, 34, 42, 49, 54, and 67 days after the administration, the survival rate of MSCs was quantitatively analyzed by in vivo bioimaging analysis.

In order to confirm the engraftment of the transplanted MSCs, the mouse was dissected 74 days after the administration, and a frozen block of the MSC-transplanted muscular tissue was prepared and immunohistologically stained. MSCs engrafted in the muscular tissue were detected by DAB staining (VECTASTAIN Elite ABC, Vector Laboratories, Inc.) using an antibody against luciferase introduced in the MSCs (rabbit anti-firefly Luciferase antibody, $\frac{1}{100}$ diluted, Abcam Plc.) and subsequent H & E staining. The number of MSCs per unit area was counted to calculate an engraftment rate.

(Results)

1. Gene Transduction of MSCs with AAV Vector and Confirmation of Expression

Figures 5A, 5B:
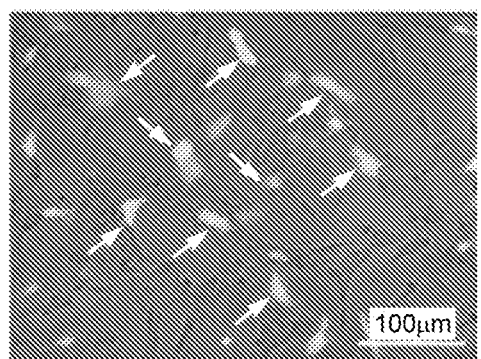
FIGS. 5A-B show the gene transfection of MSCs with an AAV vector and the expression of IL-10.

The results are shown in FIGS. 5A-B. FIG. 5A shows the results about the gene transduction of vIL-10(-)MSCs. FIG. 5B shows the results about the expression of IL-10 in vIL-10(+)MSCs.

The gene transduction was confirmed on the basis of the number of GFP-positive cells. As shown in FIG. 5A, many MSCs after the gene transduction were GFP-positive cells, demonstrating that the gene transduction of MSCs using the AAV vector is efficiency carried out. As shown in FIG. 5B, IL-10 was able to be detected in the culture supernatant of vIL-10(+)MSCs, showing that IL-10 can be highly expressed in vIL-10(+)MSCs.

Figures 6A, 6B:
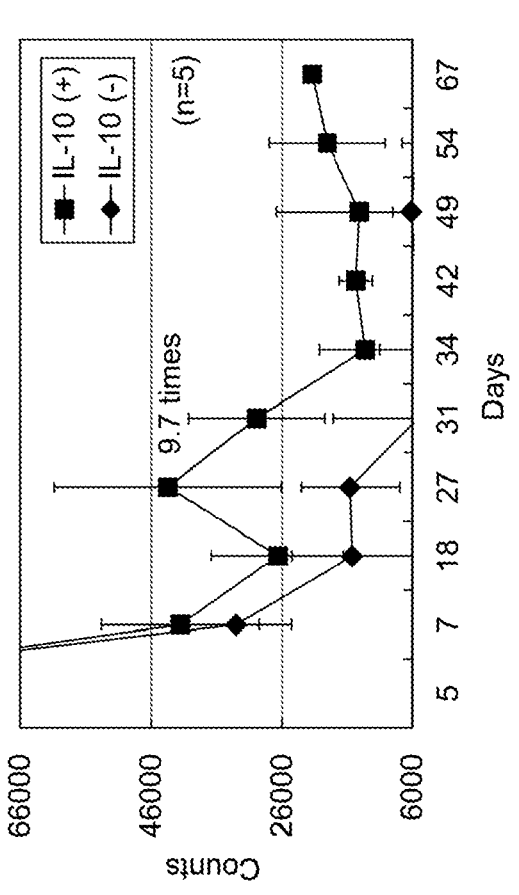
FIGS. 6A-B show the survival rate of MSCs after the stem cell for transplantation of the present invention was administered by local injection to each NOD/Scid mouse.

2. Administration by Local Injection to Mouse and Verification of Survival Rate and Engraftment Rate FIGS. 6A-B show the images of the mouse and the survival rate of MSCs. FIG. 6A shows the images of the mouse taken the indicated numbers of days after the administration of MSCs. FIG. 6B shows quantitative values (n=5) calculated on the basis of the results of FIG. 6A. The signal intensity of luciferase in vIL-10(+)MSCs 31 days after the administration exhibited a value 9.7 times higher than that of vIL-10(-)MSCs. Further surprisingly, vIL-10(+)MSCs maintained the high signal of luciferase even 67 days after the administration. Thus, significant improvement in the survival rate of MSCs was able to be confirmed. These results demonstrated that MSCs are allowed to persistently express IL-10 using the AAV vector, and can thereby survive over a long period in a tissue in which the MSCs have been transplanted.

Figure 7A:
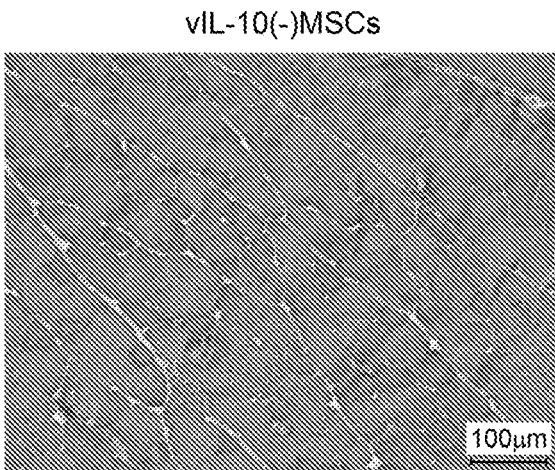
FIGS. 7A-C are diagrams showing the engraftment of transplanted MSCs in mouse muscular tissue.
Figure 7B:
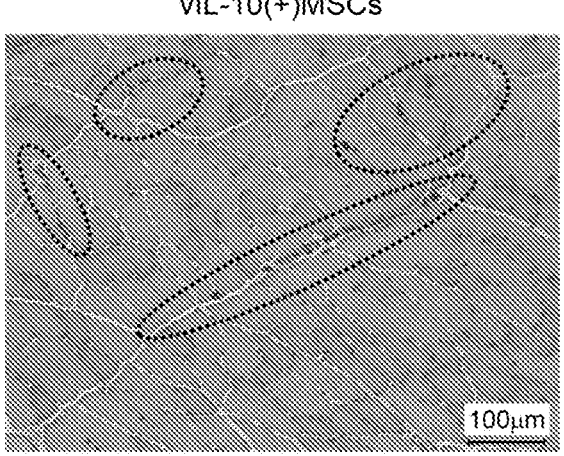
Figure 7C:
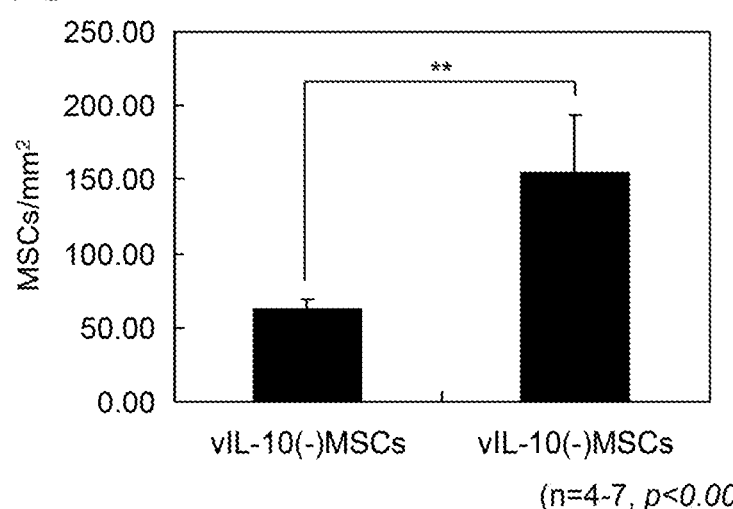

FIGS. 7A-C are diagrams showing the engraftment of MSCs in muscular tissue, which was the transplantation site. FIGS. 7A and 7B show the images of the engraftment of vIL-10(-)MSCs and vIL-10(+)MSCs, respectively, in the muscular tissue. FIG. 7C shows the engraftment rates of vIL-10(-)MSCs and vIL-10(+)MSCs calculated by measuring the number of MSCs per unit area from the images of histological staining.

vIL-10(+)MSCs are indicated by dark spots encircled by broken lines in FIG. 7B by the DAB staining, demonstrating their engraftment in the endomysium and the perimysium. The results of FIG. 7C also demonstrated that the vIL-10 (+)MSCs, which correspond to the stem cell for transplantation of the present invention, have engraftment efficiency improved by two or more times as compared with the control vIL-10(-)MSCs with a significant difference (p<0.005).

Example 3

<Verification of Improvement in Survival Rate and Engraftment Rate in Experiment of Transplantation of MSCs Transduced with IL-10 Expression AAV Vector into Dog>

(Objective)

The objective is to verify, in dogs, the effect of improving the survival and engraftment rates of AAV1-IL-10-introduced MSCs, which was demonstrated in mice.

(Method)

1. Preparation of Dog Bone Marrow-Derived MSCs

Figure 8:
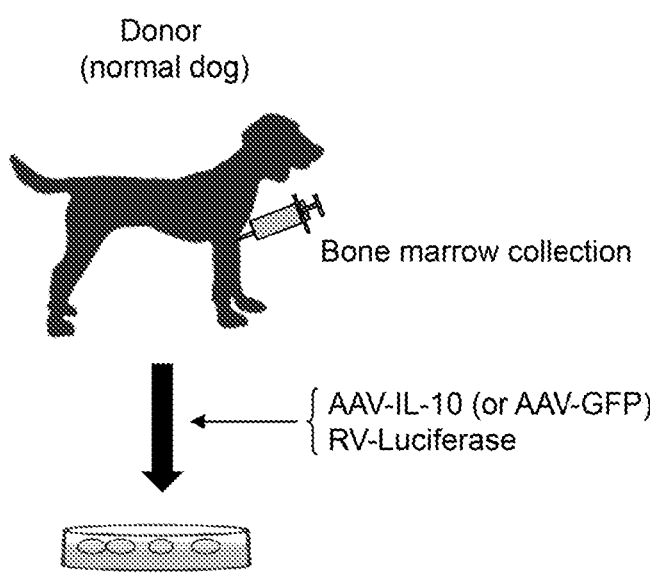
FIG. 8 is a conceptual diagram showing the flow of the transplantation of vIL-10(+)MSCs to a dog.
Figure 8:
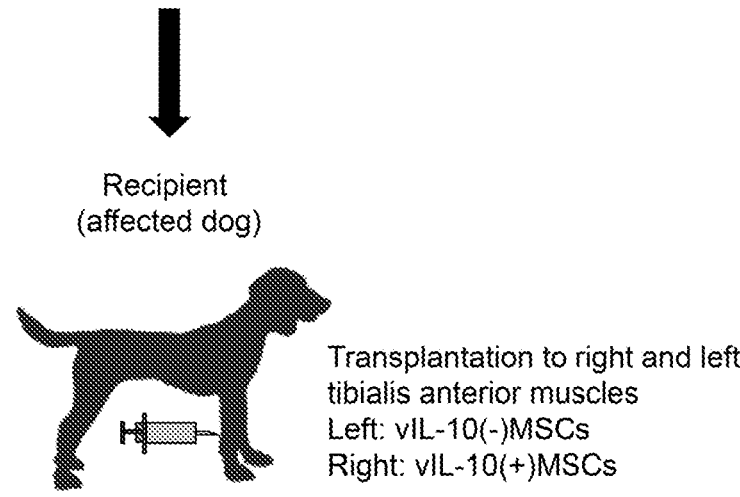

Donor and recipient dogs were selected from DLA (dog leukocyte antigen)-matched male and female pairs of beagles. As illustrated in FIG. 8, 2 mL of a bone marrow fluid was collected from the fore-leg right and left upper arms of the donor normal dog. The bone marrow fluid was cultured in 2 mL of RPMI-1640 (Life Technologies Corporation) containing 20 U/mL heparin. Monocytes were isolated ($1.3 \times 10^8$ cells) under a density gradient using Histopaque-1077 (Sigma-Aldrich Corp.). Then, a CD271-positive fraction having the high ability to grow (MSC Research Tool Box-CD271 (LNGFR) containing CD271 (LNGFR)-PE & Anti-PE Micro Beads (Miltenyi Biotec) was concentrated using immuno-magnetic beads (MACS® Columns and MACS Separators, Miltenyi Biotec) (CD271-positive cells=1.4 to $5 \times 10^6$ cells). The detailed method followed the attached protocol. The recovered cells were seeded to a 6-well plate (IWAKI/AGC Techno Glass Co., Ltd.) and cultured in nonhaematopoietic (NH) Expansion Medium (Miltenyi Biotec) supplemented with 100 U/mL penicillin and 100 μg/mL streptomycin (Sigma-Aldrich Corp.). The medium was replaced with a fresh one every 3 days, and the cells were allowed to grow into a level corresponding to ten T225 flasks through 4 passages. The detailed preparation followed Kasahara, Y., et al., 2012, Mol Ther., 20 (1): 168-77. CD271[+]MSCs were infected with a luciferase expression lentivirus vector (200 μL) in the presence of Polybrene (8 μg/mL) and cultured at $32^\circ$ C. for 2 days in NH Expansion Medium (T225 flask) for gene transfection. Subsequently, AAV1-GFP or AAV1-IL-10 ($8.0 \times 10^{12}$ g.c. each) was cultured twice at $37^\circ$ C. for 3 days

21 in the NH Expansion Medium (T225 flask). The luciferase expression in MSCs was confirmed by luciferase activity assay (Bright-Glo Luciferase Assay System, Promega K.K.), and the IL-10 expression was confirmed by ELISA analysis (canine IL-10 ELISA Kit, Thermo Fisher Scientific Inc.). Appliskan (Thermo Fisher Scientific Inc.) (luminescence, 450 nm, shake) was used in both of the measurements.

Figures 10A, 10B:
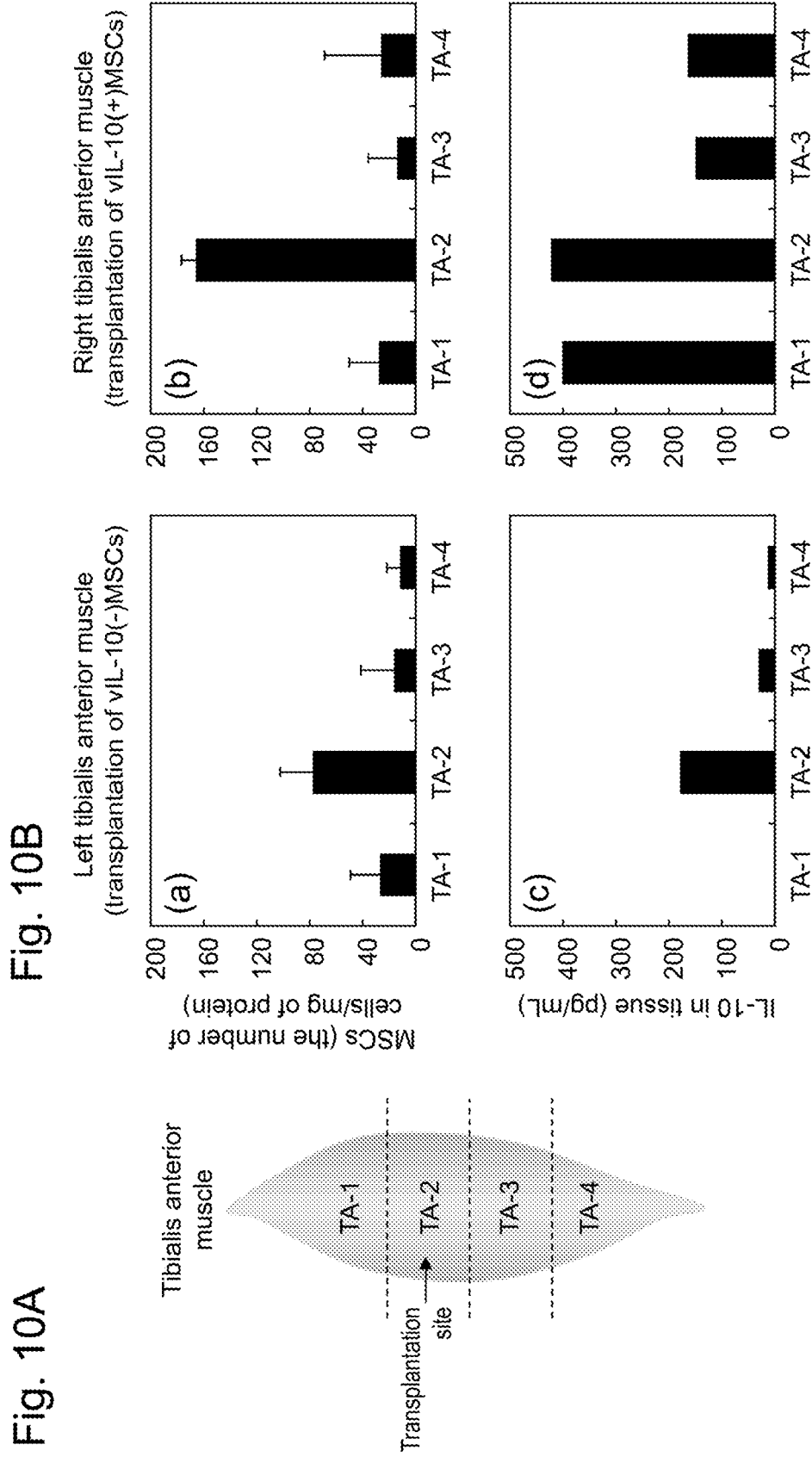
FIG. 10A shows the positions of 4 sites in MSC-transplanted right and left tibialis anterior muscle tissues. TA-2 is the transplantation site of MSCs.
FIG. 10B shows the survival rate of MSCs at each site in the right and left tibialis anterior muscle tissues and an IL-10 concentration in the tissues 30 days after the transplantation. The survival rates of MSCs in the left tibialis anterior muscle (vIL-10(−)MSCs were transplanted) and the right tibialis anterior muscle (vIL-10(+)MSCs were transplanted) are shown in (a) and (b), respectively. The IL-10 concentration in the muscular tissue of each site in the left tibialis anterior muscle and the right tibialis anterior muscle is shown in (c) and (d), respectively.

2. Allograft Transplantation to Dog and Verification of Survival Rate and Engraftment Rate of Transplanted Cells An affected dog was prepared as a recipient of the transplanted cells. In order to induce muscle injury in a normal beagle (4 years and 3 months old, male), 1.0 mL of 50 μM cardiotoxin was administered by local injection to each of the right and left tibialis anterior muscles 5 days before transplantation of MSCs to prepare an affected dog. Subsequently, the MSCs introducing each gene in the preceding paragraph "1. Preparation of dog bone marrow-derived MSCs" were recovered by trypsin treatment and then adjusted to $2.4\times10^7$ to $2.7\times10^7$ cells/2 mL PBS. Under 2% isoflurane (Japanese Pharmacopoeia) anesthesia, vIL-10 (−) MSCs were locally transplanted to the left tibialis anterior muscle of the affected dog, and vIL-10(+)MSCs were locally transplanted to the right tibialis anterior muscle thereof. During this operation, no immunosuppressant was used. One month later, the MSC-transplanted right and left tibialis anterior muscle tissues were biopsied and each sectioned into 4 sites as shown in FIG. 10A. Then, muscle extracts were obtained using a POLYTRON homogenizer (150 to 180 min$^{-1}$). The engraftment of MSCs was analyzed on the basis of the luciferase activity (Bright-Glo Luciferase Assay System) of the muscle extracts. The measurement values were corrected with the amount of tissue protein (Pierce® BCA Protein Assay Kit, Thermo Fisher Scientific Inc.). The amount of IL-10 in the tissue was calculated by ELISA analysis (canine IL-10 ELISA Kit) using the muscle extracts.

After the biopsy of the muscular tissues after the transplantation, a section was prepared as a frozen block from a part of each tissue and pathologically analyzed. MSCs engrafted in the muscular tissue were detected by DAB staining (VECTASTAIN Elite ABC, Vector Laboratories, Inc.) using an antibody against the marker luciferase introduced in the MSCs (rabbit anti-firefly Luciferase antibody, 1/100 diluted, Abcam Plc.) and subsequent H & E staining in the same way as in Example 2. The localization of the transplanted cells was further observed under a microscope (Leica, DMR). The tissue was immunohistologically stained using rabbit anti-firefly Luciferase antibody (1/50 diluted, Abcam Plc.) and mouse anti-dystrophin antibody (1/100 diluted, NCL-DYS3, Leica), and Alexa 594-conjugated anti-rabbit IgG antibodies (1/250 diluted, Life Technologies Corporation) as a secondary antibody, and enclosed in a mounting agent Vectashield Mounting Medium with DAPI (Vector Laboratories, Inc.) also serving as nucleic staining. The localization of the transplanted cells was observed under a fluorescence microscope (Olympus Corp., IX71).

(Results)

Figure 9:
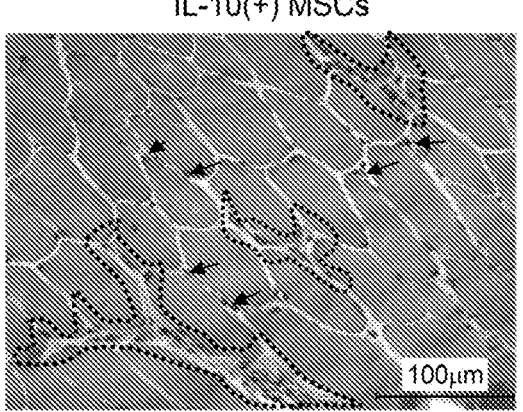
FIG. 9 is a diagram showing the engraftment of vIL-10 (+)MSCs in dog muscular tissue 30 days after transplantation. The dark spots encircled by broken lines or indicated by arrows represent vIL-10(+)MSCs engrafted in the endomysium and the perimysium.

The results are shown in FIGS. 9 to 11.

FIG. 9 shows the image of the engraftment of vIL-10(+) MSCs in the right tibialis anterior muscle tissue, which was the transplantation site, 30 days after the transplantation. The DAB-stained dark spots encircled by broken lines and indicated by arrows represent vIL-10(+)MSCs engrafted in the endomysium and the perimysium.

FIG. 10A is a diagram showing the positions of the 4 sites in the MSC-transplanted right and left tibialis anterior muscle tissues. FIG. 10B shows the survival rate of MSCs at each site in the right and left tibialis anterior muscle tissues and an IL-10 concentration in the tissues 30 days after the transplantation. In the diagram, the survival rates of vIL-10(−)MSCs (left tibialis anterior muscle tissue) and vIL-10(+)MSCs (right tibialis anterior muscle tissue) based on luciferase activity are shown in (a) and (b), respectively. The IL-10 concentration in the muscular tissue of each site in vIL-10(−)MSCs (left tibialis anterior muscle tissue) and vIL-10(+)MSCs (right tibialis anterior muscle tissue) is shown in (c) and (d), respectively. At the MSC transplantation site TA-2, vIL-10(+)MSCs were shown to have a survival rate two or more times that of vIL-10(−)MSCs. The transplantation of vIL-10(−)MSCs also increased the IL-10 concentration in the muscular tissue, whereas as a result of transplanting vIL-10(+)MSCs, a high concentration of IL-10 was able to be confirmed not only at the transplantation site but at neighboring sites thereof. No rise was confirmed in IL-10 concentration in serum (not shown). These results are consistent with the results about mice demonstrated in Example 2 and demonstrated that the vIL-10(+)MSCs, which correspond to the stem cell for transplantation of the present invention, also have a high post-transplantation survival rate and engraftment rate in dogs. This suggested that the stem cell for transplantation of the present invention is effective regardless of organism species.

Figures 11A, 11B:
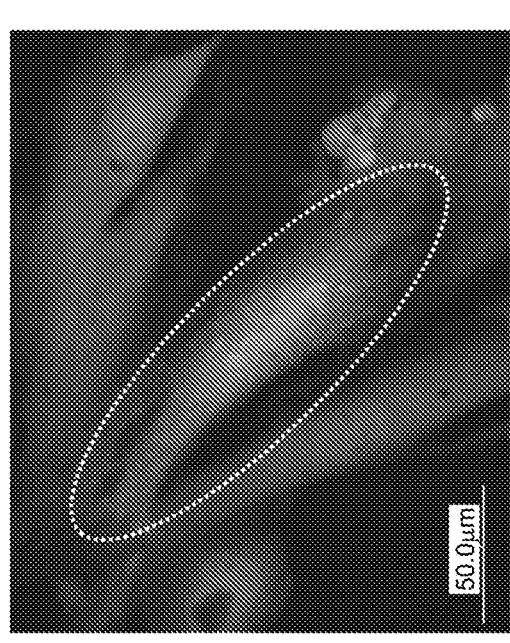
FIGS. 11A-B show the engraftment and myofiber formation of non-differentiation-induced MSCs.

FIGS. 11A-B shows the engraftment and myofiber formation of non-differentiation-induced MSCs. FIG. 11A shows the pathologic image of MSCs in the muscular tissue. FIG. 11B shows the ability of MSCs to be fused with myotube cells in vitro. As a result of administering vIL-10 (+)MSCs twice to the right tibialis anterior muscle of the recipient dog and conducting long-term observation, the transplanted vIL-10(+)MSCs, as shown in FIG. 11A, were shown to be engrafted at the inflammation site (arrows encircled by broken lines). In FIG. 11A, the arrowheads represent newly formed myofibers. As shown in FIG. 11B, the fusion between MSCs and myoblasts (bright cells encircled by a broken line) was able to be confirmed in vitro. These results indicate that the stem cell for transplantation of the present invention can be allowed to persistently express IL-10 and engrafted in muscular tissue for a long period, thereby newly reforming myofibers through the fusion with neighboring myoblasts. Adverse events such as hematopoietic injury or tumor formation were not observed.

Example 4

<Verification of Induction of Acquired Immunological Tolerance Using MSCs—(1)>

(Objective)

The objective is to verify, in dogs, that immunological tolerance against immunogen to be introduced to recipient individual is induced by pretreatment using MSCs.

(Method)

The basic method followed the method described in Example 3.

1. Immunological Tolerance Induction Procedures

On the basis of the method for inducing immunological tolerance of the present invention, the immunological tolerance was induced by the following procedures: first, AAV9 was introduced as an immunogen to each recipient, and this administration date was defined as a reference date (day 0). Next, 8 days before the reference date, MSCs and the immunogen AAV9 were intravenously administered as the first step of the method for inducing immunological tolerance. For a control, only AAV9 or only MSCs were intravenously administered. Subsequently, on the day before the reference date, MSCs were intravenously administered as the second step of the method for inducing immunological tolerance. This administration was not carried out for the control. On the reference date, the immunogen AAV9 was introduced by local administration. The introduced AAV9 causes luciferase gene expression. Only an AAV9-free PBS buffer was introduced to the control. 4 weeks after the introduction, biopsy was conducted.

2. Preparation of Dog Bone Marrow-Derived MSCs

The basic method followed the method described in Example 3.

3. Preparation of AAV9-Luc

The luciferase expression AAV vector (AAV9-CAG-Luc: in the present specification, also referred to as "AAV9-Luc") introduced and administered as an immunogen in this Example was prepared on the basis of the method described in the paragraph "1. Preparation of recombinant AAV" of Comparative Example 2.

The AAV9-Luc was prepared according to the method described in Ohshima S., et al., 2009, Mol Ther, 17 (1): 73-80 or Shin J. H., et al., 2011, Gene Ther, 18: 910-919. The AAV9-Luc is capable of persistently expressing luciferase in a tissue that has received it.

4. Verification of Induction of Immunological Tolerance by Local Administration

The recipients used were normal beagles (2-month-old male or female littermates). According to the preceding paragraph "1. Immunological tolerance induction procedures", 8 days before the reference date, $4 \times 10^6$ cells ($1 \times 10^6$ cells/kg B.W.) of MSCs and 2 mL of an AAV9-Luc solution were locally administered using a syringe to the tibialis anterior muscle of each dog (MSCs+AAV) for immunological tolerance induction. For a control, only AAV9-Luc (Cont–AAV) or only MSCs (Cont-MSCs) were administered. On the day before the reference date, MSCs were administered at $1.8 \times 10^6$ cells/kg B.W. to the individual MSCs+AAV or Cont-MSCs. On the reference date, introduction to the tibialis anterior muscle was carried out using a syringe such that AAV9-Luc was locally administered at $1 \times 10^{12}$ v.g. (solution volume: 2 mL) per site to two sites in the individual MSCs+AAV or Cont–AAV, and 2 mL of a PBS buffer alone was locally administered to each of two sites in the individual Cont-MSCs. 4 weeks after the reference date, the tibialis anterior muscle was biopsied at the introduction sites. The tissue was immunohistologically stained using an antibody against luciferase (rabbit anti-firefly Luciferase antibody, 1:2000 diluted, Abcam Plc.) and Alexa 594-conjugated anti-rabbit IgG antibodies (1:1000 diluted, Life Technologies Corporation) as a secondary antibody. The expression of luciferase was observed under a fluorescence microscope (Olympus Corp., IX71).

(Results)

Figure 12A:
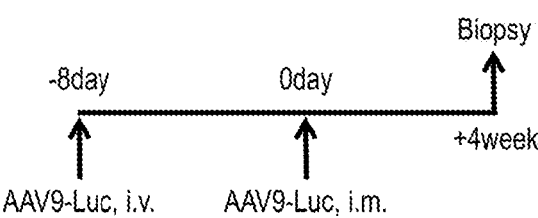
FIGS. 12A-C are diagrams showing the effect of inducing immunological tolerance by the method for inducing acquired immunological tolerance of the present invention.
Figure 12A:
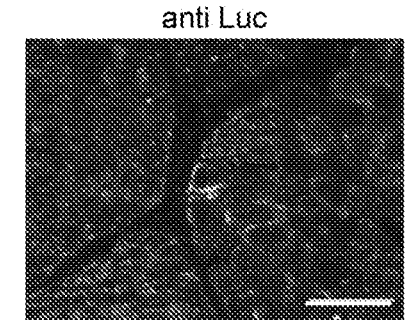
Figure 12B:
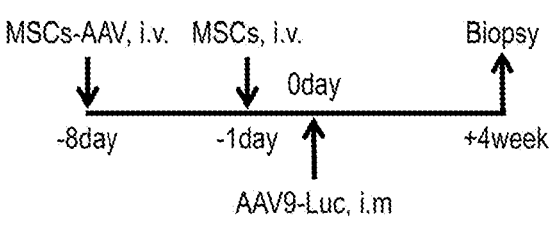
Figure 12B:
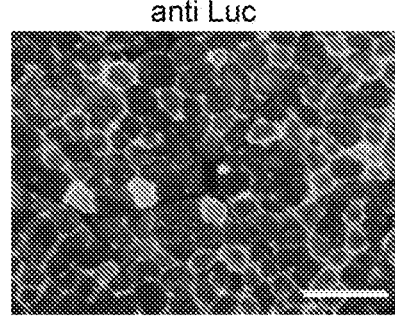
Figure 12C:
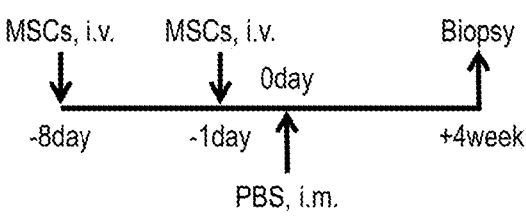
Figure 12C:
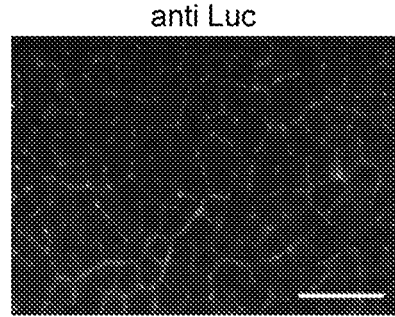

The results are shown in FIGS. 12A-C. FIG. 12A shows the results about Cont–AAV. FIG. 12B shows the results about MSCs+AAV. FIG. 12C shows the results about Cont-MSCs. In the MSCs+AAV treated by the method for inducing immunological tolerance of the present invention, the expression of the marker gene of luciferase derived from the immunogen AAV9 was observed (FIG. 12B). By contrast, in the Cont–AAV pretreated with only AAV9 without the immunological tolerance induction treatment with MSCs, the expression of luciferase was not seen (FIG. 12A). Likewise, in the Cont-MSCs that underwent neither administration nor introduction of AAV9-Luc, the expression of luciferase was not seen (FIG. 12C).

These results indicate that immunological tolerance against the immunogen AAV9-Luc was induced in the individual that received the immunological induction treatment by the method of the present invention, and the introduced AAV9-Luc was not eradicated by immune response even 4 weeks after the introduction of the AAV9-Luc.

Example 5

<Verification of Induction of Acquired Immunological Tolerance Using MSCs—(2)>

(Objective)

The objective is to verify that in the introduction of an immunogen according to the method for inducing acquired immunological tolerance of the present invention, even intravenous introduction produces effects similar to those of local introduction.

(Method)

1. Immunological Tolerance Induction Procedures

The basic procedures followed the procedures of Example 4. In this Example, AAV9-Luc or AAV-µDys was introduced as an immunogen.

2. Human-Derived MSCs

Human-derived bone marrow-derived cells (JCR Pharmaceuticals Co., Ltd.) were purchased and then expanded by culture for use.

3. Preparation of AAV9-µDys

The AAV9-µDys to be introduced and administered was prepared on the basis of the method described in the paragraph "1. Preparation of recombinant AAV" of Comparative Example 2.

The microdystrophin expression AAV vector (AAV9-CMV-µDys; in the present specification, also referred to as "AAV9-µDys") was prepared according to the AAV9-Luc preparation method described in the paragraph 3 of Example 4. Microdystrophin is a truncated form of the dystrophin gene developed so as to permit integration into an AAV vector, and has the same functions as those of the dystrophin gene. The AAV9-µDys is capable of persistently expressing microdystrophin in a tissue that has received it.

4. Verification of Induction of Immunological Tolerance by Intravenous Introduction The recipients used were two 11-week-old littermates of normal beagles (male) or one Duchenne dystrophy-affected dog (male) (CXMD$_J$). The CXMD$_J$ is a hybrid that has been bred and maintained by crossing the sperm of a golden retriever spontaneous Duchenne dystrophy-affected dog (GRMD) imported from abroad with a beagle in the National Center of Neurology and Psychiatry (Japan) (Shimatsu Y. et al., 2005, Acta Myol vol. 24 (2): 145-54; Yugeta N. et al., 2006, BMC Cardiovasc Disord, 6: 47; and Kobayashi M et al., 2009, Muscle Nerve, 40 (5): 815-26).

According to the preceding paragraph "1. Immunological tolerance induction procedures", 8 days before the reference date, $1 \times 10^6$ cells/kg B.W. of MSCs and 3 mL of AAV9-Luc were intravenously injected to each normal beagle (MSCs+AAV-Luc), and $1 \times 10^6$ cells/kg B.W. of MSCs and 3 mL of AAV9-µDys were intravenously injected to the affected dog (DMD/MSCs+AAV-µDys), for immunological tolerance induction. For a control, only AAV9-Luc (Cont–AAV) was administered. Each amount of AAV was set to $5 \times 10^5$ v.g./cell. On the day before the reference date, $2 \times 10^6$ cells/kg B.W. of MSCs were administered to the individual MSCs+AAV-Luc or DMD/MSCs+AAV-µDys. On the reference date, $2 \times 10^{12}$ v.g./kg B.W. of AAV9-Luc was intravenously introduced to the individual MSCs+AAV-Luc or Cont–AAV, and $2 \times 10^{12}$ v.g./kg B.W. of AAV9-µDys was intravenously introduced to the DMD/MSCs+AAV-µDys (solution volume: 3 mL each). 4 weeks after the reference date, the temporal muscle was excised from each dog and biopsied. The tissue was immunohistologically stained using an antibody against luciferase (rabbit anti-firefly Luciferase antibody, 1:2000 diluted, Abcam Plc.) and an antibody against dystrophin (mouse anti-dystrophin antibody, 1:50 diluted, NCL-DYS3, Leica), and Alexa 594-conjugated anti-rabbit IgG antibodies (1:1000 diluted, Life Technologies Corporation) as a secondary antibody, and enclosed in a mounting agent Vectashield Mounting Medium with DAPI (Vector Laboratories, Inc.) also serving as nucleic staining. The expression of luciferase or microdystrophin was observed under a fluorescence microscope (Olympus Corp., IX71).
(Results)

Figure 13A:
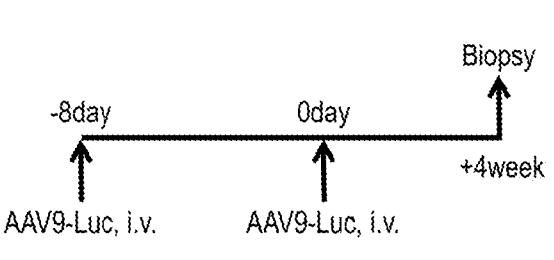
FIGS. 13A-C are diagrams showing the effect of inducing immunological tolerance by the method for inducing acquired immunological tolerance of the present invention using intravenous administration.
Figure 13A:
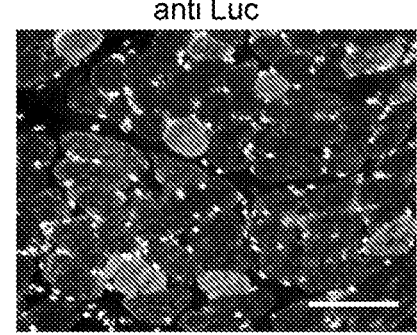
Figure 13B:
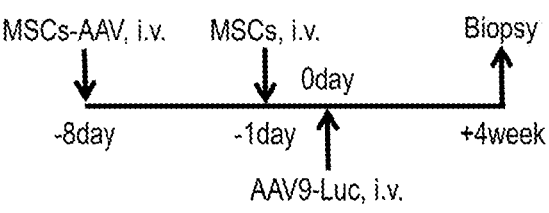
Figure 13C:
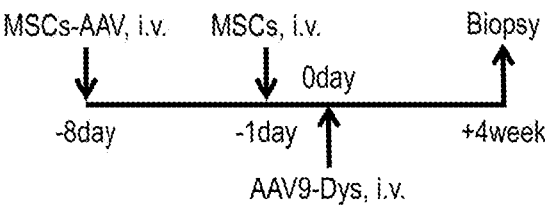
Figure 13C:
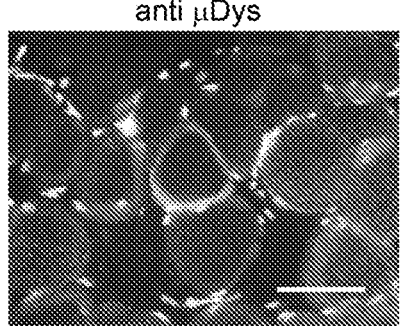

The results are shown in FIGS. 13A-C. FIG. 13A shows the results about Cont–AAV. FIG. 13B shows the results about MSCs+AAV-Luc. FIG. 13C shows the results about DMD/MSCs+AAV-μDys. In the MSCs+AAV-Luc treated by the method for inducing immunological tolerance of the present invention, the expression of luciferase was observed (FIG. 13B), as in Example 4. By contrast, in the Cont–AAV pretreated with only AAV9 without the immunological tolerance induction treatment with MSCs, the expression of luciferase was not seen (FIG. 13A). These results demonstrated that in the introduction of an immunogen by immunological tolerance induction treatment, not only local introduction but systemic administration mediated by the circulatory system, such as intravenous introduction, produces similar effects.

In the DMD/MSCs+AAV–μDys, the expression of microdystrophin was confirmed (FIG. 13C), as in the MSCs+AAV-Luc given luciferase. These results indicate that immunological tolerance against the immunogen AAV9-μDys was induced, and the introduced AAV9-μDys was not eradicated by immune response even 4 weeks after the introduction of the AAV9-μDys.

Example 6

<Verification of Gene Therapy by Method for Inducing Acquired Immunological Tolerance>
(Objective)

The objective is to verify the effect of gene therapy on an AAV9-μDys-introduced individual using the method for inducing acquired immunological tolerance of the present invention.
(Method)
1. Preparation of Various Dogs 11-week-old littermates of normal beagles (Normal), muscular dystrophy-affected dogs (DMD), and treated affected dogs (DMD/MSCs+AAV–μDys) in which AAV9-μDys was introduced to the affected dogs using the method for inducing acquired immunological tolerance of the present invention, were prepared. The DMD is the aforementioned CXMD_J affected dog. The DMD/MSCs+AAV-μDys is the AAV9-μDys-introduced affected dog prepared in Example 5.

2. Verification of Effect of Gene Therapy—(1)

A 15-meter running test was conducted using each dog, and its running time was measured. As for DMD, only one measurement was carried out for 5 individuals at each weekly age. As for Normal and DMD/MSCs+AAV-μDys, 4 measurements were carried out per individual, and an average time thereof was calculated.
3. Verification of Effect of Gene Therapy—(2)

The pathological evaluation of muscular dystrophy followed the Grading Score (ver. 10) used in the National Center of Neurology and Psychiatry (Japan). In this Grading Score, regarding muscular dystrophy-related pathological conditions of 14 items [eating/swallowing, drinking, salivation, dysphagia, abnormal phonation, test of getting up from a lying position, playfulness, gait, hindlimb gaiting test, seated posture, temporal muscle atrophy, sublingual swelling, macroglossia, and thigh muscle], appropriate statuses were selected from those specified in each item, and scores assigned in advance to the statuses were summed up for scoring. A larger score means more severe symptoms. The pathological evaluation was conducted once a month.
(Results)

Figure 14:
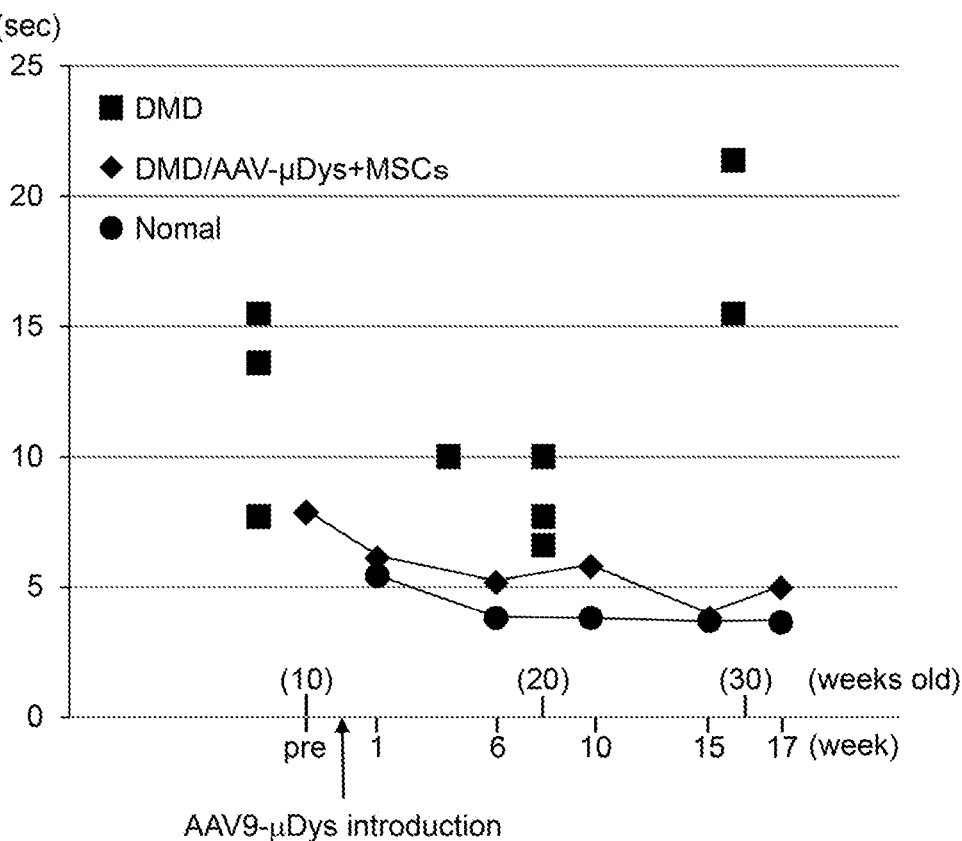
FIG. 14 is a diagram showing results about the running times of various dogs in a 15-meter running test. In the diagram, "pre" in the lower tier of the abscissa represents the point in time when a muscular dystrophy-affected dog (DMD) was pretreated by the method for inducing acquired immunological tolerance of the present invention. Other numeric values represent the length of time (week) that passed from the reference date at which AAV9-μDys was introduced. The numeric values within the parentheses in the upper tier of the abscissa represent the weekly age of the muscular dystrophy-affected dog (DMD).

The results of the 15-meter running test are shown in FIG. 14. Change in Grading Score as the pathological evaluation of muscular dystrophy is shown in FIG. 15.

As seen from FIG. 14, the gene therapy-untreated muscular dystrophy-affected dogs (DMD) had a slower running time than that of the normal individuals (Nomal) at every weekly age, showing motor dysfunction. By contrast, the muscular dystrophy-treated affected dogs (DMD/MSCs+AAV-μDys) subjected to the immunological tolerance induction treatment and given AAV9-μDys using the method for inducing acquired immunological tolerance of the present invention had a running time closer to that of the normal individuals, as compared with the running time of DMD. This effect was also maintained even 17 weeks after the introduction of AAV9-μDys.

Figure 15:
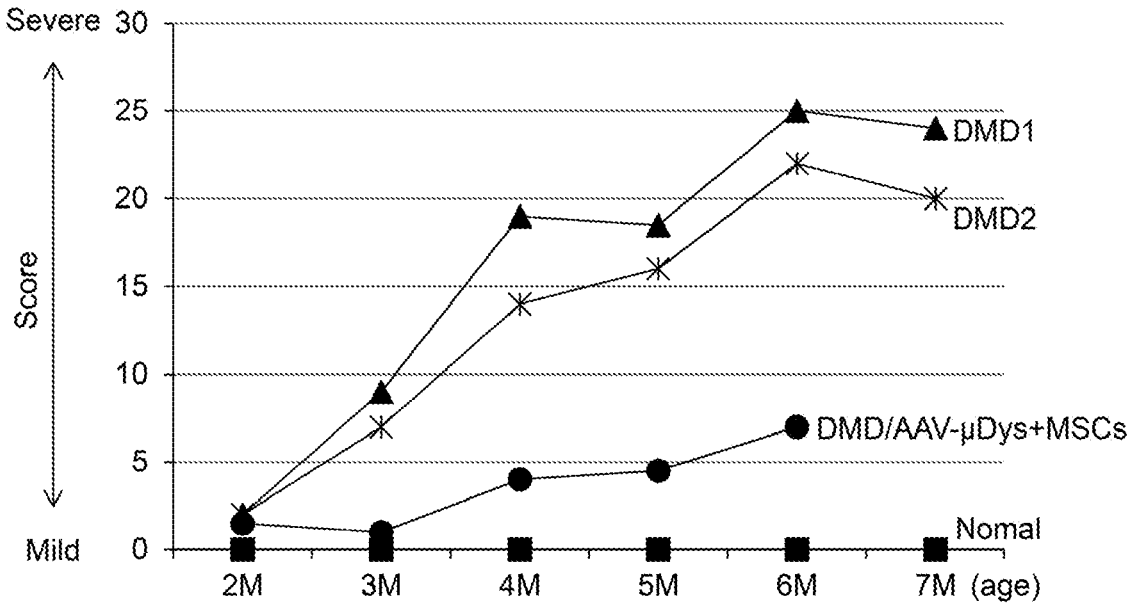
FIG. 15 is a diagram showing the pathological evaluation of each muscular dystrophy-affected dog. The ordinate shows a score of the Grading Score, and the abscissa shows the age (months old) of the affected dog.

The results of the pathological evaluation of muscular dystrophy are shown in FIG. 15. As seen from FIG. 15, the symptoms of the gene therapy-untreated muscular dystrophy-affected dogs (DMD1 and DMD2) progressed and became more severe with increases in monthly age. By contrast, the symptoms of the muscular dystrophy-treated affected dogs (DMD/MSCs+AAV-μDys) given AAV9-μDys using the method for inducing acquired immunological tolerance of the present invention progressed very slowly even with increases in monthly age, as compared with DMD.

These results indicate that the treatment of a recipient by the method for inducing acquired immunological tolerance of the present invention allows gene therapy to maintain its effects over long period without eradicating the introduced AAV9-μDys by immune response.

All publications, patents, and patent applications cited herein are incorporated herein by reference in their entirety.

---

The invention claimed is:

1. A method for inducing acquired immunological tolerance in a subject to an immunogen, wherein the immunogen is an AAV9 vector, the method comprising:

a first step of administering systemically to the subject a human mesenchymal stem cell (hMSC) and the immunogen, wherein the hMSC is administered on the day before or the very day of administering the immunogen; and, after a predetermined number of days, a second step of administering systemically to the subject a human MSC and the immunogen, wherein a hMSC is administered on the day before or the very day of administering the immunogen, whereby an immune response to the immunogen in the subject is suppressed.

2. The method of claim 1, wherein the hMSC overexpresses interleukin-10 (IL-10).

3. The method of claim 2, wherein the overexpression of IL-10 is overexpression of an exogenous IL-10 expression system.

4. The method of claim 1, wherein the hMSC does not overexpress IL-10.

5. The method of claim 1, wherein the systemic administration is intravenous administration.

6. The method of claim 1, wherein the AAV9 vector is a microdystrophin expression AAV9 vector.

* * * * *